United States Patent
Meyers

(10) Patent No.: US 6,759,222 B2
(45) Date of Patent: Jul. 6, 2004

(54) 14815, A HUMAN KINASE FAMILY MEMBER AND USES THEREFOR

(75) Inventor: Rachel E. Meyers, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/335,711

(22) Filed: Jan. 2, 2003

(65) Prior Publication Data

US 2003/0134317 A1 Jul. 17, 2003

Related U.S. Application Data

(60) Provisional application No. 60/345,853, filed on Jan. 2, 2002.

(51) Int. Cl.$^7$ .......................... C12N 9/12; C12N 15/00; C12N 5/00; C12Q 1/68; C07H 21/04
(52) U.S. Cl. ........................ 435/194; 435/6; 435/252.3; 435/320.1; 435/325; 536/23.2
(58) Field of Search .................. 536/23.2; 435/194, 435/6, 252.3, 320.1, 325

(56) References Cited

FOREIGN PATENT DOCUMENTS

| WO | WO 01/55318 A2 | 8/2001 |
|---|---|---|
| WO | WO 01/66594 A2 | 9/2001 |
| WO | WO 02/33095 A2 | 4/2002 |

OTHER PUBLICATIONS

Isogai, T., et al., "*Homo sapiens* cDNA FIJ32685 fis, clone TESTI2000154, weakly similar to Putative Serine/Threonine–Protein Kinase D1044.3 in Chromosome III (EC 2.7.1–)", (Aug. 1, 2002), (sequence) GenBank [online] Bethesda, MD, USA: National Center for Biotechnology Information [retrieved on Dec. 10, 2003]. Retrieved from the Internet: URL: http://www.ncbi.nlm.nih.gov/>. GenBank Accession No. AK057247.

Sugano, S. and Suzuki, Y., "*Homo sapiens* cDNA FLJ25966 fis, clone TST05207", (Sep. 12, 2003) (sequence) GenBank [online] Bethesda, MD, USA: National Center for Biotechnology Information [retrieved on Dec. 10, 2003]. Retrieved from the Internet: URL: http://www.ncbi.nlm.nih.gov/>. GenBank Accession No. AK098832.

*Primary Examiner*—Maryam Monshipouri
(74) *Attorney, Agent, or Firm*—Millennium Pharmaceuticals, Inc.

(57) ABSTRACT

The invention provides isolated nucleic acids molecules, designated 14815 nucleic acid molecules, which encode novel kinase family members. The invention also provides antisense nucleic acid molecules, recombinant expression vectors containing 14815 nucleic acid molecules, host cells into which the expression vectors have been introduced, and nonhuman transgenic animals in which a 14815 gene has been introduced or disrupted. The invention still further provides isolated 14815 proteins, fusion proteins, antigenic peptides and anti-14815 antibodies. Diagnostic and therapeutic methods utilizing compositions of the invention are also provided.

15 Claims, 1 Drawing Sheet

SEQUENCE LISTING

```
<160> NUMBER OF SEQ ID NOS: 12

<210> SEQ ID NO 1
<211> LENGTH: 3919
<212> TYPE: DNA
<213> ORGANISM: Homo sapiens
<220> FEATURE:
<221> NAME/KEY: CDS
<222> LOCATION: (183)...(3530)
<220> FEATURE:
<221> NAME/KEY: misc_feature
<222> LOCATION: 3899
<223> OTHER INFORMATION: n=a, t, c, or g

<400> SEQUENCE: 1
gacgggctga gactggacgg gaccccggt  ctgcagcagc aggtgacagc agcagggaca      60
atgataagga gattggcctg aaggagggac cgtccctccc gcgcgaaaag tcagaaatgg     120
ccaatgaagc ttttgcttat aaaaggaatg cgatgttaat tctggggcat tgatgtttta    180 ca atg cct gat caa gat aaa aag gtg aag acc aca gaa aaa tca act         227
   Met Pro Asp Gln Asp Lys Lys Val Lys Thr Thr Glu Lys Ser Thr
   1               5                  10                  15 gat aaa cag caa gaa atc acc atc agg gac tat tca gat ctt aaa aga       275
Asp Lys Gln Gln Glu Ile Thr Ile Arg Asp Tyr Ser Asp Leu Lys Arg
                20                  25                  30 ctt cgg tgc ctt ttg aac gtc caa tca agc aaa caa cag ctt cca gcc       323
Leu Arg Cys Leu Leu Asn Val Gln Ser Ser Lys Gln Gln Leu Pro Ala
            35                  40                  45 att aac ttc gat agt gcc caa aat agc atg acg aag tct gag ccc gcc       371
Ile Asn Phe Asp Ser Ala Gln Asn Ser Met Thr Lys Ser Glu Pro Ala
        50                  55                  60 atc agg gcg ggt gga cac aga gct cgg ggt cag tgg cat gaa tcc aca       419
Ile Arg Ala Gly Gly His Arg Ala Arg Gly Gln Trp His Glu Ser Thr
    65                  70                  75 gaa gct gtt gaa ctt gaa aat ttt agt ata aac tac aag aat gag aga       467
Glu Ala Val Glu Leu Glu Asn Phe Ser Ile Asn Tyr Lys Asn Glu Arg
80                  85                  90                  95 aat ttc agc aaa cat cct cag cgt aaa cta ttt cag gag atc ttt acc       515
Asn Phe Ser Lys His Pro Gln Arg Lys Leu Phe Gln Glu Ile Phe Thr
                100                 105                 110 gcc ttg gtg aaa aat aga ctc ata agc aga gag tgg gtt aat cga gcc       563
Ala Leu Val Lys Asn Arg Leu Ile Ser Arg Glu Trp Val Asn Arg Ala
```

-continued

```
                 115                 120                 125
cca tct att cat ttt ctg aga gtg tta atc tgt ctg agg cta cta atg         611
Pro Ser Ile His Phe Leu Arg Val Leu Ile Cys Leu Arg Leu Leu Met
            130                 135                 140 agg gat cca tgt tat cag gaa ata ctc cat agc ttg ggt ggg att gaa         659
Arg Asp Pro Cys Tyr Gln Glu Ile Leu His Ser Leu Gly Gly Ile Glu
        145                 150                 155 aac cta gct cag tat atg gag att gta gcc aat gag tac ctc ggc tat         707
Asn Leu Ala Gln Tyr Met Glu Ile Val Ala Asn Glu Tyr Leu Gly Tyr
160                 165                 170                 175 gga gaa gag cag cac act gtg gac aag ctg gtc aac atg aca tat att         755
Gly Glu Glu Gln His Thr Val Asp Lys Leu Val Asn Met Thr Tyr Ile
                180                 185                 190 ttt caa aaa ctt gct gca gtc aaa gat caa aga gaa tgg gtc acc aca         803
Phe Gln Lys Leu Ala Ala Val Lys Asp Gln Arg Glu Trp Val Thr Thr
            195                 200                 205 agt gga gcc cac aag aca tta gta aat tta ctt ggt gcc cga gat act         851
Ser Gly Ala His Lys Thr Leu Val Asn Leu Leu Gly Ala Arg Asp Thr
        210                 215                 220 aat gtt cta ttg ggt tcc ctt ctg gct ctg gct agt tta gca gaa agt         899
Asn Val Leu Leu Gly Ser Leu Leu Ala Leu Ala Ser Leu Ala Glu Ser
225                 230                 235 caa gaa tgt agg gag aag ata agt gaa ctc aac att gta gaa aat ctg         947
Gln Glu Cys Arg Glu Lys Ile Ser Glu Leu Asn Ile Val Glu Asn Leu
240                 245                 250                 255 ttg atg att tta cat gaa tat gac ttg ctt tct aaa aga cta aca gcg         995
Leu Met Ile Leu His Glu Tyr Asp Leu Leu Ser Lys Arg Leu Thr Ala
                260                 265                 270 gag ttg ctg cgc cta ctt tgt gca gag ccc cag gtg aaa gag cag gtg        1043
Glu Leu Leu Arg Leu Leu Cys Ala Glu Pro Gln Val Lys Glu Gln Val
            275                 280                 285 aag ctc tat gag ggg ata ccg gtc ctc ctc agt ctg ctc cac tct gac        1091
Lys Leu Tyr Glu Gly Ile Pro Val Leu Leu Ser Leu Leu His Ser Asp
        290                 295                 300 cac ttg aag ctc ctc tgg agc att gtc tgg att ctg gta cag gtt tgt        1139
His Leu Lys Leu Leu Trp Ser Ile Val Trp Ile Leu Val Gln Val Cys
305                 310                 315 gag gac cct gag acc agc gtg gaa att cgc att tgg gga ggc atc aaa        1187
Glu Asp Pro Glu Thr Ser Val Glu Ile Arg Ile Trp Gly Gly Ile Lys
320                 325                 330                 335 cag ctt ctt cat att tta caa gga gac aga aat ttt gtt tct gat cac        1235
Gln Leu Leu His Ile Leu Gln Gly Asp Arg Asn Phe Val Ser Asp His
                340                 345                 350 tcc tcc att gga agc ctg tcc agt gca aat gct gca ggc cga atc cag        1283
Ser Ser Ile Gly Ser Leu Ser Ser Ala Asn Ala Ala Gly Arg Ile Gln
            355                 360                 365 cag ctt cat tta tca gaa gac ttg agc cct agg gaa ata caa gaa aat        1331
Gln Leu His Leu Ser Glu Asp Leu Ser Pro Arg Glu Ile Gln Glu Asn
        370                 375                 380 act ttc tca ctt caa gca gcc tgc tgt gct gcc ctc act gag ctg gtg        1379
Thr Phe Ser Leu Gln Ala Ala Cys Cys Ala Ala Leu Thr Glu Leu Val
385                 390                 395 ctc aat gac acc aat gcc cac cag gtg gtt cag gaa aat ggt gta tat        1427
Leu Asn Asp Thr Asn Ala His Gln Val Val Gln Glu Asn Gly Val Tyr
400                 405                 410                 415 aca ata gca aaa tta att tta cca aat aag caa aag aat gca gca aaa        1475
Thr Ile Ala Lys Leu Ile Leu Pro Asn Lys Gln Lys Asn Ala Ala Lys
                420                 425                 430 agt aat cta tta cag tgt tat gct ttc aga gcc ttg aga ttt ctc ttc        1523
```

```
                Ser Asn Leu Leu Gln Cys Tyr Ala Phe Arg Ala Leu Arg Phe Leu Phe
                            435                 440                 445 agt atg gaa aga aac aga cca ctc ttt aaa aga ctt ttc ccc aca gac                 1571
Ser Met Glu Arg Asn Arg Pro Leu Phe Lys Arg Leu Phe Pro Thr Asp
        450                 455                 460 ttg ttt gag atc ttc att gac ata ggg cat tat gta cgt gat atc agt                 1619
Leu Phe Glu Ile Phe Ile Asp Ile Gly His Tyr Val Arg Asp Ile Ser
465                 470                 475 gct tat gaa gaa ttg gta tcc aag ctg aat tta tta gtg gag gat gaa                 1667
Ala Tyr Glu Glu Leu Val Ser Lys Leu Asn Leu Leu Val Glu Asp Glu
480                 485                 490                 495 ctg aag caa att gct gaa aat att gaa agc att aat cag aac aaa gct                 1715
Leu Lys Gln Ile Ala Glu Asn Ile Glu Ser Ile Asn Gln Asn Lys Ala
                500                 505                 510 cct tcg aaa tat ata ggc aac tat gca att ttg gat cat ctt gga agt                 1763
Pro Ser Lys Tyr Ile Gly Asn Tyr Ala Ile Leu Asp His Leu Gly Ser
            515                 520                 525 gga gct ttt ggc tgt gtt tac aag gtt aga aag cat agt ggt caa aat                 1811
Gly Ala Phe Gly Cys Val Tyr Lys Val Arg Lys His Ser Gly Gln Asn
        530                 535                 540 ctt tta gca atg aaa gag gtc aat tta cat aac cca gca ttt gga aag                 1859
Leu Leu Ala Met Lys Glu Val Asn Leu His Asn Pro Ala Phe Gly Lys
545                 550                 555 gat aag aaa gat cga gac agc agc gta agg aat att gtt tct gaa tta                 1907
Asp Lys Lys Asp Arg Asp Ser Ser Val Arg Asn Ile Val Ser Glu Leu
560                 565                 570                 575 aca ata att aaa gag cag ctt tat cat ccc aac att gta cgt tat tac                 1955
Thr Ile Ile Lys Glu Gln Leu Tyr His Pro Asn Ile Val Arg Tyr Tyr
                580                 585                 590 aaa aca ttt ctg gaa aac gat agg ttg tac ata gtt atg gag ctg ata                 2003
Lys Thr Phe Leu Glu Asn Asp Arg Leu Tyr Ile Val Met Glu Leu Ile
            595                 600                 605 gaa gga gcc ccg ctt gga gag cat ttc agt tct ttg aag gaa aaa cat                 2051
Glu Gly Ala Pro Leu Gly Glu His Phe Ser Ser Leu Lys Glu Lys His
        610                 615                 620 cac cat ttt act gaa gaa aga cta tgg aaa ata ttt ata cag ctg tgc                 2099
His His Phe Thr Glu Glu Arg Leu Trp Lys Ile Phe Ile Gln Leu Cys
625                 630                 635 tta gct ctt cga tac tta cac aag gag aag agg att gtc cat aga gat                 2147
Leu Ala Leu Arg Tyr Leu His Lys Glu Lys Arg Ile Val His Arg Asp
640                 645                 650                 655 ctg aca cca aac aac att atg ttg ggg gat aag gac aaa gta aca gtt                 2195
Leu Thr Pro Asn Asn Ile Met Leu Gly Asp Lys Asp Lys Val Thr Val
                660                 665                 670 act gac ttt ggc ctg gca aag caa aaa caa gaa aac agt aaa ctc acg                 2243
Thr Asp Phe Gly Leu Ala Lys Gln Lys Gln Glu Asn Ser Lys Leu Thr
            675                 680                 685 tct gtg gtt gga aca atc ctg tat tct tgc ccc gag gta ctg aag agt                 2291
Ser Val Val Gly Thr Ile Leu Tyr Ser Cys Pro Glu Val Leu Lys Ser
        690                 695                 700 gag ccg tat ggg gag aag gct gat gtc tgg gca gta ggc tgc atc ctt                 2339
Glu Pro Tyr Gly Glu Lys Ala Asp Val Trp Ala Val Gly Cys Ile Leu
705                 710                 715 tat cag atg gcg act ttg agt ccc ccc ttc tac agc act aac atg ctg                 2387
Tyr Gln Met Ala Thr Leu Ser Pro Pro Phe Tyr Ser Thr Asn Met Leu
720                 725                 730                 735 tcc ttg gct aca aaa ata gtg gag gcg gta tat gaa cca gtg cca gaa                 2435
Ser Leu Ala Thr Lys Ile Val Glu Ala Val Tyr Glu Pro Val Pro Glu
                740                 745                 750
```

```
ggt atc tac tct gaa aaa gta aca gac acc atc agc agg tgc ctc act    2483
Gly Ile Tyr Ser Glu Lys Val Thr Asp Thr Ile Ser Arg Cys Leu Thr
            755                 760                 765 cct gat gcg gaa gct cgt cca gat att gta gaa gtc agt tcg atg ata    2531
Pro Asp Ala Glu Ala Arg Pro Asp Ile Val Glu Val Ser Ser Met Ile
770                 775                 780 tca gat gtc atg atg aaa tat tta gac aac tta tct aca tcc cag ttg    2579
Ser Asp Val Met Met Lys Tyr Leu Asp Asn Leu Ser Thr Ser Gln Leu
        785                 790                 795 tcc ttg gaa aag aag cta gaa cgg gaa cga aga cgc aca caa agg tat    2627
Ser Leu Glu Lys Lys Leu Glu Arg Glu Arg Arg Arg Thr Gln Arg Tyr
800                 805                 810                 815 ttt atg gaa gcc aac cgg aac acc gtc aca tgt cac cat gag ctg gct    2675
Phe Met Glu Ala Asn Arg Asn Thr Val Thr Cys His His Glu Leu Ala
                820                 825                 830 gtt cta tct cac gag acc ttt gag aag gca agt ttg agt agc agc agc    2723
Val Leu Ser His Glu Thr Phe Glu Lys Ala Ser Leu Ser Ser Ser Ser
            835                 840                 845 agt gga gca gcc agc ctg aaa agt gaa ctt tca gaa agc gca gac ctg    2771
Ser Gly Ala Ala Ser Leu Lys Ser Glu Leu Ser Glu Ser Ala Asp Leu
        850                 855                 860 ccc cct gaa ggc ttc cag gcc tcc tat ggt aaa gac gaa gac agg gcc    2819
Pro Pro Glu Gly Phe Gln Ala Ser Tyr Gly Lys Asp Glu Asp Arg Ala
865                 870                 875 tgt gac gaa atc ctg tca gat gat aac ttc aac ctg gaa aat gct gag    2867
Cys Asp Glu Ile Leu Ser Asp Asp Asn Phe Asn Leu Glu Asn Ala Glu
880                 885                 890                 895 aaa gat aca tat tca gag gta gat gat gaa ttg gac att tcg gat aac    2915
Lys Asp Thr Tyr Ser Glu Val Asp Asp Glu Leu Asp Ile Ser Asp Asn
                900                 905                 910 tcc agc agc tcc agt tca agc cct ctg aaa gaa tct aca ttc aac att    2963
Ser Ser Ser Ser Ser Ser Pro Leu Lys Glu Ser Thr Phe Asn Ile
            915                 920                 925 tta aag aga agt ttt agt gct tca gga gga gaa aga caa tcc caa aca    3011
Leu Lys Arg Ser Phe Ser Ala Ser Gly Gly Glu Arg Gln Ser Gln Thr
        930                 935                 940 agg gac ttc act gga gga aca gga tca aga cca aga cca gca tca gca    3059
Arg Asp Phe Thr Gly Gly Thr Gly Ser Arg Pro Arg Pro Ala Ser Ala
945                 950                 955 gga att gct gtg tcc cag agg aaa gtc cgt cag atc agt gat cct att    3107
Gly Ile Ala Val Ser Gln Arg Lys Val Arg Gln Ile Ser Asp Pro Ile
960                 965                 970                 975 cag cag ata tta att cag ctg cac aaa ata atc tat atc aca cag ctt    3155
Gln Gln Ile Leu Ile Gln Leu His Lys Ile Ile Tyr Ile Thr Gln Leu
                980                 985                 990 cct cca gct ttg cac cac aat ttg aaa aga agg gtt ata gag aga ttc    3203
Pro Pro Ala Leu His His Asn Leu Lys Arg Arg Val Ile Glu Arg Phe
            995                 1000                1005 aag aaa tcc ctc ttc agc cag cag agt aac cct tgt aat ttg aaa tct    3251
Lys Lys Ser Leu Phe Ser Gln Gln Ser Asn Pro Cys Asn Leu Lys Ser
        1010                1015                1020 gaa att aaa aag tta tct cag gga tct cca gaa ccg att gag ccc aac    3299
Glu Ile Lys Lys Leu Ser Gln Gly Ser Pro Glu Pro Ile Glu Pro Asn
1025                1030                1035 ttt ttc aca gca gat tac cat tta tta cat cgt tca tcc ggt gga aac    3347
Phe Phe Thr Ala Asp Tyr His Leu Leu His Arg Ser Ser Gly Gly Asn
                1040                1045                1050                1055 agc ctg tcc cca aat gac cct aca ggt tta cca acc agc att gaa ttg    3395
Ser Leu Ser Pro Asn Asp Pro Thr Gly Leu Pro Thr Ser Ile Glu Leu
            1060                1065                1070
```

```
gag gaa gga ata aca tat gaa cag atg cag act gtg att gaa gaa gtc      3443
Glu Glu Gly Ile Thr Tyr Glu Gln Met Gln Thr Val Ile Glu Glu Val
            1075                1080                1085 ctt gag gaa agt ggc tat tac aat ttt aca tct aac agg tat cat tcc      3491
Leu Glu Glu Ser Gly Tyr Tyr Asn Phe Thr Ser Asn Arg Tyr His Ser
        1090                1095                1100 tat cca tgg ggg acc aag aat cac cca acc aaa aga tga aaatgctgca       3540
Tyr Pro Trp Gly Thr Lys Asn His Pro Thr Lys Arg  *
    1105                1110                1115 ttttgagtgg acttgatttt ctcagtgaag ttcaagttct ggacttcagc cgctattgca    3600
agatgcccaa ggattgggtg ctgctagagg gtgtggaaaa gaccaagatg ccatggggcc    3660
tgcaggactt ctttctgggg gtcctgtgct ggagtatatg acagctgcgg tacttgaggg    3720
cttcattgcc agaacacatt atatacagga tgtcagagct accagtgtgc tgctgggaga    3780
aaatgctgca aaattcatct tttgagggt gggggaaaa cccaaaaaca acaacaaaaa      3840
aactctctta cagaattttc cttaacatta aaaaaaactt gtcatatttt tcaaaggcnc    3900
atttgatact cagaattgc                                                  3919

<210> SEQ ID NO 2
<211> LENGTH: 1115
<212> TYPE: PRT
<213> ORGANISM: Homo sapiens

<400> SEQUENCE: 2

Met Pro Asp Gln Asp Lys Lys Val Lys Thr Thr Glu Lys Ser Thr Asp
  1               5                  10                  15

Lys Gln Gln Glu Ile Thr Ile Arg Asp Tyr Ser Asp Leu Lys Arg Leu
             20                  25                  30

Arg Cys Leu Leu Asn Val Gln Ser Ser Lys Gln Gln Leu Pro Ala Ile
         35                  40                  45

Asn Phe Asp Ser Ala Gln Asn Ser Met Thr Lys Ser Glu Pro Ala Ile
     50                  55                  60

Arg Ala Gly Gly His Arg Ala Arg Gly Gln Trp His Glu Ser Thr Glu
 65                  70                  75                  80

Ala Val Glu Leu Glu Asn Phe Ser Ile Asn Tyr Lys Asn Glu Arg Asn
                 85                  90                  95

Phe Ser Lys His Pro Gln Arg Lys Leu Phe Gln Glu Ile Phe Thr Ala
            100                 105                 110

Leu Val Lys Asn Arg Leu Ile Ser Arg Glu Trp Val Asn Arg Ala Pro
        115                 120                 125

Ser Ile His Phe Leu Arg Val Leu Ile Cys Leu Arg Leu Leu Met Arg
    130                 135                 140

Asp Pro Cys Tyr Gln Glu Ile Leu His Ser Leu Gly Ile Glu Asn
145                 150                 155                 160

Leu Ala Gln Tyr Met Glu Ile Val Ala Asn Glu Tyr Leu Gly Tyr Gly
                165                 170                 175

Glu Glu Gln His Thr Val Asp Lys Leu Val Asn Met Thr Tyr Ile Phe
            180                 185                 190

Gln Lys Leu Ala Ala Val Lys Asp Gln Arg Glu Trp Val Thr Thr Ser
        195                 200                 205

Gly Ala His Lys Thr Leu Val Asn Leu Leu Gly Ala Arg Asp Thr Asn
    210                 215                 220

Val Leu Leu Gly Ser Leu Leu Ala Leu Ala Ser Leu Ala Glu Ser Gln
225                 230                 235                 240
```

-continued

```
Glu Cys Arg Glu Lys Ile Ser Glu Leu Asn Ile Val Glu Asn Leu Leu
            245                 250                 255
Met Ile Leu His Glu Tyr Asp Leu Leu Ser Lys Arg Leu Thr Ala Glu
            260                 265                 270
Leu Leu Arg Leu Leu Cys Ala Glu Pro Gln Val Lys Glu Gln Val Lys
            275                 280                 285
Leu Tyr Glu Gly Ile Pro Val Leu Leu Ser Leu His Ser Asp His
            290                 295                 300
Leu Lys Leu Leu Trp Ser Ile Val Trp Ile Leu Val Gln Val Cys Glu
305                 310                 315                 320
Asp Pro Glu Thr Ser Val Glu Ile Arg Ile Trp Gly Gly Ile Lys Gln
            325                 330                 335
Leu Leu His Ile Leu Gln Gly Asp Arg Asn Phe Val Ser Asp His Ser
            340                 345                 350
Ser Ile Gly Ser Leu Ser Ser Ala Asn Ala Ala Gly Arg Ile Gln Gln
            355                 360                 365
Leu His Leu Ser Glu Asp Leu Ser Pro Arg Glu Ile Gln Glu Asn Thr
            370                 375                 380
Phe Ser Leu Gln Ala Ala Cys Cys Ala Ala Leu Thr Glu Leu Val Leu
385                 390                 395                 400
Asn Asp Thr Asn Ala His Gln Val Val Gln Glu Asn Gly Val Tyr Thr
            405                 410                 415
Ile Ala Lys Leu Ile Leu Pro Asn Lys Gln Lys Asn Ala Ala Lys Ser
            420                 425                 430
Asn Leu Leu Gln Cys Tyr Ala Phe Arg Ala Leu Arg Phe Leu Phe Ser
            435                 440                 445
Met Glu Arg Asn Arg Pro Leu Phe Lys Arg Leu Phe Pro Thr Asp Leu
            450                 455                 460
Phe Glu Ile Phe Ile Asp Ile Gly His Tyr Val Arg Asp Ile Ser Ala
465                 470                 475                 480
Tyr Glu Glu Leu Val Ser Lys Leu Asn Leu Leu Val Glu Asp Glu Leu
            485                 490                 495
Lys Gln Ile Ala Glu Asn Ile Glu Ser Ile Asn Gln Asn Lys Ala Pro
            500                 505                 510
Ser Lys Tyr Ile Gly Asn Tyr Ala Ile Leu Asp His Leu Gly Ser Gly
            515                 520                 525
Ala Phe Gly Cys Val Tyr Lys Val Arg Lys His Ser Gly Gln Asn Leu
            530                 535                 540
Leu Ala Met Lys Glu Val Asn Leu His Asn Pro Ala Phe Gly Lys Asp
545                 550                 555                 560
Lys Lys Asp Arg Asp Ser Ser Val Arg Asn Ile Val Ser Glu Leu Thr
            565                 570                 575
Ile Ile Lys Glu Gln Leu Tyr His Pro Asn Ile Val Arg Tyr Tyr Lys
            580                 585                 590
Thr Phe Leu Glu Asn Asp Arg Leu Tyr Ile Val Met Glu Leu Ile Glu
            595                 600                 605
Gly Ala Pro Leu Gly Glu His Phe Ser Ser Leu Lys Glu Lys His His
            610                 615                 620
His Phe Thr Glu Glu Arg Leu Trp Lys Ile Phe Ile Gln Leu Cys Leu
625                 630                 635                 640
Ala Leu Arg Tyr Leu His Lys Glu Lys Arg Ile Val His Arg Asp Leu
            645                 650                 655
```

-continued

```
Thr Pro Asn Asn Ile Met Leu Gly Asp Lys Asp Lys Val Thr Val Thr
            660                 665                 670
Asp Phe Gly Leu Ala Lys Gln Lys Gln Glu Asn Ser Lys Leu Thr Ser
            675                 680                 685
Val Val Gly Thr Ile Leu Tyr Ser Cys Pro Glu Val Leu Lys Ser Glu
            690                 695                 700
Pro Tyr Gly Glu Lys Ala Asp Val Trp Ala Val Gly Cys Ile Leu Tyr
705                 710                 715                 720
Gln Met Ala Thr Leu Ser Pro Pro Phe Tyr Ser Thr Asn Met Leu Ser
            725                 730                 735
Leu Ala Thr Lys Ile Val Glu Ala Val Tyr Glu Pro Val Pro Glu Gly
            740                 745                 750
Ile Tyr Ser Glu Lys Val Thr Asp Thr Ile Ser Arg Cys Leu Thr Pro
            755                 760                 765
Asp Ala Glu Ala Arg Pro Asp Ile Val Glu Val Ser Ser Met Ile Ser
            770                 775                 780
Asp Val Met Met Lys Tyr Leu Asp Asn Leu Ser Thr Ser Gln Leu Ser
785                 790                 795                 800
Leu Glu Lys Lys Leu Glu Arg Glu Arg Arg Thr Gln Arg Tyr Phe
            805                 810                 815
Met Glu Ala Asn Arg Asn Thr Val Thr Cys His His Glu Leu Ala Val
            820                 825                 830
Leu Ser His Glu Thr Phe Glu Lys Ala Ser Leu Ser Ser Ser Ser Ser
            835                 840                 845
Gly Ala Ala Ser Leu Lys Ser Glu Leu Ser Glu Ser Ala Asp Leu Pro
            850                 855                 860
Pro Glu Gly Phe Gln Ala Ser Tyr Gly Lys Asp Glu Asp Arg Ala Cys
865                 870                 875                 880
Asp Glu Ile Leu Ser Asp Asp Phe Asn Leu Glu Asn Ala Glu Lys
            885                 890                 895
Asp Thr Tyr Ser Glu Val Asp Asp Glu Leu Asp Ile Ser Asp Asn Ser
            900                 905                 910
Ser Ser Ser Ser Ser Ser Pro Leu Lys Glu Ser Thr Phe Asn Ile Leu
            915                 920                 925
Lys Arg Ser Phe Ser Ala Ser Gly Glu Arg Gln Ser Gln Thr Arg
            930                 935                 940
Asp Phe Thr Gly Gly Thr Gly Ser Arg Pro Arg Pro Ala Ser Ala Gly
945                 950                 955                 960
Ile Ala Val Ser Gln Arg Lys Val Arg Gln Ile Ser Asp Pro Ile Gln
            965                 970                 975
Gln Ile Leu Ile Gln Leu His Lys Ile Tyr Ile Thr Gln Leu Pro
            980                 985                 990
Pro Ala Leu His His Asn Leu Lys Arg Arg Val Ile Glu Arg Phe Lys
            995                 1000                1005
Lys Ser Leu Phe Ser Gln Gln Ser Asn Pro Cys Asn Leu Lys Ser Glu
            1010                1015                1020
Ile Lys Lys Leu Ser Gln Gly Ser Pro Glu Pro Ile Glu Pro Asn Phe
1025                1030                1035                1040
Phe Thr Ala Asp Tyr His Leu Leu His Arg Ser Ser Gly Gly Asn Ser
            1045                1050                1055
Leu Ser Pro Asn Asp Pro Thr Gly Leu Pro Thr Ser Ile Glu Leu Glu
            1060                1065                1070
Glu Gly Ile Thr Tyr Glu Gln Met Gln Thr Val Ile Glu Glu Val Leu
```

```
                   1075                1080                 1085
Glu Glu Ser Gly Tyr Tyr Asn Phe Thr Ser Asn Arg Tyr His Ser Tyr
       1090                1095                1100

Pro Trp Gly Thr Lys Asn His Pro Thr Lys Arg
1105                1110                1115

<210> SEQ ID NO 3
<211> LENGTH: 3348
<212> TYPE: DNA
<213> ORGANISM: Homo sapiens
<220> FEATURE:
<221> NAME/KEY: CDS
<222> LOCATION: (1)...(3348)

<400> SEQUENCE: 3 atg cct gat caa gat aaa aag gtg aag acc aca gaa aaa tca act gat        48
Met Pro Asp Gln Asp Lys Lys Val Lys Thr Thr Glu Lys Ser Thr Asp
1               5                   10                  15 aaa cag caa gaa atc acc atc agg gac tat tca gat ctt aaa aga ctt        96
Lys Gln Gln Glu Ile Thr Ile Arg Asp Tyr Ser Asp Leu Lys Arg Leu
            20                  25                  30 cgg tgc ctt ttg aac gtc caa tca agc aaa caa cag ctt cca gcc att       144
Arg Cys Leu Leu Asn Val Gln Ser Ser Lys Gln Gln Leu Pro Ala Ile
        35                  40                  45 aac ttc gat agt gcc caa aat agc atg acg aag tct gag ccc gcc atc       192
Asn Phe Asp Ser Ala Gln Asn Ser Met Thr Lys Ser Glu Pro Ala Ile
    50                  55                  60 agg gcg ggt gga cac aga gct cgg ggt cag tgg cat gaa tcc aca gaa       240
Arg Ala Gly Gly His Arg Ala Arg Gly Gln Trp His Glu Ser Thr Glu
65                  70                  75                  80 gct gtt gaa ctt gaa aat ttt agt ata aac tac aag aat gag aga aat       288
Ala Val Glu Leu Glu Asn Phe Ser Ile Asn Tyr Lys Asn Glu Arg Asn
                85                  90                  95 ttc agc aaa cat cct cag cgt aaa cta ttt cag gag atc ttt acc gcc       336
Phe Ser Lys His Pro Gln Arg Lys Leu Phe Gln Glu Ile Phe Thr Ala
            100                 105                 110 ttg gtg aaa aat aga ctc ata agc aga gag tgg gtt aat cga gcc cca       384
Leu Val Lys Asn Arg Leu Ile Ser Arg Glu Trp Val Asn Arg Ala Pro
        115                 120                 125 tct att cat ttt ctg aga gtg tta atc tgt ctg agg cta cta atg agg       432
Ser Ile His Phe Leu Arg Val Leu Ile Cys Leu Arg Leu Leu Met Arg
    130                 135                 140 gat cca tgt tat cag gaa ata ctc cat agc ttg ggt ggg att gaa aac       480
Asp Pro Cys Tyr Gln Glu Ile Leu His Ser Leu Gly Gly Ile Glu Asn
145                 150                 155                 160 cta gct cag tat atg gag att gta gcc aat gag tac ctc ggc tat gga       528
Leu Ala Gln Tyr Met Glu Ile Val Ala Asn Glu Tyr Leu Gly Tyr Gly
                165                 170                 175 gaa gag cag cac act gtg gac aag ctg gtc aac atg aca tat att ttt       576
Glu Glu Gln His Thr Val Asp Lys Leu Val Asn Met Thr Tyr Ile Phe
            180                 185                 190 caa aaa ctt gct gca gtc aaa gat caa aga gaa tgg gtc acc aca agt       624
Gln Lys Leu Ala Ala Val Lys Asp Gln Arg Glu Trp Val Thr Thr Ser
        195                 200                 205 gga gcc cac aag aca tta gta aat tta ctt ggt gcc cga gat act aat       672
Gly Ala His Lys Thr Leu Val Asn Leu Leu Gly Ala Arg Asp Thr Asn
    210                 215                 220 gtt cta ttg ggt tcc ctt ctg gct ctg gct agt tta gca gaa agt caa       720
Val Leu Leu Gly Ser Leu Leu Ala Leu Ala Ser Leu Ala Glu Ser Gln
225                 230                 235                 240
```

-continued

| | |
|---|---|
| gaa tgt agg gag aag ata agt gaa ctc aac att gta gaa aat ctg ttg<br>Glu Cys Arg Glu Lys Ile Ser Glu Leu Asn Ile Val Glu Asn Leu Leu<br>245 250 255 | 768 |
| atg att tta cat gaa tat gac ttg ctt tct aaa aga cta aca gcg gag<br>Met Ile Leu His Glu Tyr Asp Leu Leu Ser Lys Arg Leu Thr Ala Glu<br>260 265 270 | 816 |
| ttg ctg cgc cta ctt tgt gca gag ccc cag gtg aaa gag cag gtg aag<br>Leu Leu Arg Leu Leu Cys Ala Glu Pro Gln Val Lys Glu Gln Val Lys<br>275 280 285 | 864 |
| ctc tat gag ggg ata ccg gtc ctc ctc agt ctg ctc cac tct gac cac<br>Leu Tyr Glu Gly Ile Pro Val Leu Leu Ser Leu Leu His Ser Asp His<br>290 295 300 | 912 |
| ttg aag ctc ctc tgg agc att gtc tgg att ctg gta cag gtt tgt gag<br>Leu Lys Leu Leu Trp Ser Ile Val Trp Ile Leu Val Gln Val Cys Glu<br>305 310 315 320 | 960 |
| gac cct gag acc agc gtg gaa att cgc att tgg gga ggc atc aaa cag<br>Asp Pro Glu Thr Ser Val Glu Ile Arg Ile Trp Gly Gly Ile Lys Gln<br>325 330 335 | 1008 |
| ctt ctt cat att tta caa gga gac aga aat ttt gtt tct gat cac tcc<br>Leu Leu His Ile Leu Gln Gly Asp Arg Asn Phe Val Ser Asp His Ser<br>340 345 350 | 1056 |
| tcc att gga agc ctg tcc agt gca aat gct gca ggc cga atc cag cag<br>Ser Ile Gly Ser Leu Ser Ser Ala Asn Ala Ala Gly Arg Ile Gln Gln<br>355 360 365 | 1104 |
| ctt cat tta tca gaa gac ttg agc cct agg gaa ata caa gaa aat act<br>Leu His Leu Ser Glu Asp Leu Ser Pro Arg Glu Ile Gln Glu Asn Thr<br>370 375 380 | 1152 |
| ttc tca ctt caa gca gcc tgc tgt gct gcc ctc act gag ctg gtg ctc<br>Phe Ser Leu Gln Ala Ala Cys Cys Ala Ala Leu Thr Glu Leu Val Leu<br>385 390 395 400 | 1200 |
| aat gac acc aat gcc cac cag gtg gtt cag gaa aat ggt gta tat aca<br>Asn Asp Thr Asn Ala His Gln Val Val Gln Glu Asn Gly Val Tyr Thr<br>405 410 415 | 1248 |
| ata gca aaa tta att tta cca aat aag caa aag aat gca gca aaa agt<br>Ile Ala Lys Leu Ile Leu Pro Asn Lys Gln Lys Asn Ala Ala Lys Ser<br>420 425 430 | 1296 |
| aat cta tta cag tgt tat gct ttc aga gcc ttg aga ttt ctc ttc agt<br>Asn Leu Leu Gln Cys Tyr Ala Phe Arg Ala Leu Arg Phe Leu Phe Ser<br>435 440 445 | 1344 |
| atg gaa aga aac aga cca ctc ttt aaa aga ctt ttc ccc aca gac ttg<br>Met Glu Arg Asn Arg Pro Leu Phe Lys Arg Leu Phe Pro Thr Asp Leu<br>450 455 460 | 1392 |
| ttt gag atc ttc att gac ata ggg cat tat gta cgt gat atc agt gct<br>Phe Glu Ile Phe Ile Asp Ile Gly His Tyr Val Arg Asp Ile Ser Ala<br>465 470 475 480 | 1440 |
| tat gaa gaa ttg gta tcc aag ctg aat tta tta gtg gag gat gaa ctg<br>Tyr Glu Glu Leu Val Ser Lys Leu Asn Leu Leu Val Glu Asp Glu Leu<br>485 490 495 | 1488 |
| aag caa att gct gaa aat att gaa agc att aat cag aac aaa gct cct<br>Lys Gln Ile Ala Glu Asn Ile Glu Ser Ile Asn Gln Asn Lys Ala Pro<br>500 505 510 | 1536 |
| tcg aaa tat ata ggc aac tat gca att ttg gat cat ctt gga agt gga<br>Ser Lys Tyr Ile Gly Asn Tyr Ala Ile Leu Asp His Leu Gly Ser Gly<br>515 520 525 | 1584 |
| gct ttt ggc tgt gtt tac aag gtt aga aag cat agt ggt caa aat ctt<br>Ala Phe Gly Cys Val Tyr Lys Val Arg Lys His Ser Gly Gln Asn Leu<br>530 535 540 | 1632 |
| tta gca atg aaa gag gtc aat tta cat aac cca gca ttt gga aag gat<br>Leu Ala Met Lys Glu Val Asn Leu His Asn Pro Ala Phe Gly Lys Asp<br>545 550 555 560 | 1680 |

-continued

```
aag aaa gat cga gac agc agc gta agg aat att gtt tct gaa tta aca    1728
Lys Lys Asp Arg Asp Ser Ser Val Arg Asn Ile Val Ser Glu Leu Thr
            565                 570                 575 ata att aaa gag cag ctt tat cat ccc aac att gta cgt tat tac aaa    1776
Ile Ile Lys Glu Gln Leu Tyr His Pro Asn Ile Val Arg Tyr Tyr Lys
        580                 585                 590 aca ttt ctg gaa aac gat agg ttg tac ata gtt atg gag ctg ata gaa    1824
Thr Phe Leu Glu Asn Asp Arg Leu Tyr Ile Val Met Glu Leu Ile Glu
    595                 600                 605 gga gcc ccg ctt gga gag cat ttc agt tct ttg aag gaa aaa cat cac    1872
Gly Ala Pro Leu Gly Glu His Phe Ser Ser Leu Lys Glu Lys His His
610                 615                 620 cat ttt act gaa gaa aga cta tgg aaa ata ttt ata cag ctg tgc tta    1920
His Phe Thr Glu Glu Arg Leu Trp Lys Ile Phe Ile Gln Leu Cys Leu
625                 630                 635                 640 gct ctt cga tac tta cac aag gag aag agg att gtc cat aga gat ctg    1968
Ala Leu Arg Tyr Leu His Lys Glu Lys Arg Ile Val His Arg Asp Leu
                645                 650                 655 aca cca aac aac att atg ttg ggg gat aag gac aaa gta aca gtt act    2016
Thr Pro Asn Asn Ile Met Leu Gly Asp Lys Asp Lys Val Thr Val Thr
            660                 665                 670 gac ttt ggc ctg gca aag caa aaa caa gaa aac agt aaa ctc acg tct    2064
Asp Phe Gly Leu Ala Lys Gln Lys Gln Glu Asn Ser Lys Leu Thr Ser
        675                 680                 685 gtg gtt gga aca atc ctg tat tct tgc ccc gag gta ctg aag agt gag    2112
Val Val Gly Thr Ile Leu Tyr Ser Cys Pro Glu Val Leu Lys Ser Glu
    690                 695                 700 ccg tat ggg gag aag gct gat gtc tgg gca gta ggc tgc atc ctt tat    2160
Pro Tyr Gly Glu Lys Ala Asp Val Trp Ala Val Gly Cys Ile Leu Tyr
705                 710                 715                 720 cag atg gcg act ttg agt ccc ccc ttc tac agc act aac atg ctg tcc    2208
Gln Met Ala Thr Leu Ser Pro Pro Phe Tyr Ser Thr Asn Met Leu Ser
                725                 730                 735 ttg gct aca aaa ata gtg gag gcg gta tat gaa cca gtg cca gaa ggt    2256
Leu Ala Thr Lys Ile Val Glu Ala Val Tyr Glu Pro Val Pro Glu Gly
            740                 745                 750 atc tac tct gaa aaa gta aca gac acc atc agc agg tgc ctc act cct    2304
Ile Tyr Ser Glu Lys Val Thr Asp Thr Ile Ser Arg Cys Leu Thr Pro
        755                 760                 765 gat gcg gaa gct cgt cca gat att gta gaa gtc agt tcg atg ata tca    2352
Asp Ala Glu Ala Arg Pro Asp Ile Val Glu Val Ser Ser Met Ile Ser
    770                 775                 780 gat gtc atg atg aaa tat tta gac aac tta tct aca tcc cag ttg tcc    2400
Asp Val Met Met Lys Tyr Leu Asp Asn Leu Ser Thr Ser Gln Leu Ser
785                 790                 795                 800 ttg gaa aag aag cta gaa cgg gaa cga aga cgc aca caa agg tat ttt    2448
Leu Glu Lys Lys Leu Glu Arg Glu Arg Arg Arg Thr Gln Arg Tyr Phe
                805                 810                 815 atg gaa gcc aac cgg aac acc gtc aca tgt cac cat gag ctg gct gtt    2496
Met Glu Ala Asn Arg Asn Thr Val Thr Cys His His Glu Leu Ala Val
            820                 825                 830 cta tct cac gag acc ttt gag aag gca agt ttg agt agc agc agc agt    2544
Leu Ser His Glu Thr Phe Glu Lys Ala Ser Leu Ser Ser Ser Ser Ser
        835                 840                 845 gga gca gcc agc ctg aaa agt gaa ctt tca gaa agc gca gac ctg ccc    2592
Gly Ala Ala Ser Leu Lys Ser Glu Leu Ser Glu Ser Ala Asp Leu Pro
    850                 855                 860 cct gaa ggc ttc cag gcc tcc tat ggt aaa gac gaa gac agg gcc tgt    2640
Pro Glu Gly Phe Gln Ala Ser Tyr Gly Lys Asp Glu Asp Arg Ala Cys
```

```
                                         -continued 865            870           875             880
gac gaa atc ctg tca gat gat aac ttc aac ctg gaa aat gct gag aaa    2688
Asp Glu Ile Leu Ser Asp Asp Asn Phe Asn Leu Glu Asn Ala Glu Lys
                885                 890                 895 gat aca tat tca gag gta gat gat gaa ttg gac att tcg gat aac tcc    2736
Asp Thr Tyr Ser Glu Val Asp Asp Glu Leu Asp Ile Ser Asp Asn Ser
            900                 905                 910 agc agc tcc agt tca agc cct ctg aaa gaa tct aca ttc aac att tta    2784
Ser Ser Ser Ser Ser Ser Pro Leu Lys Glu Ser Thr Phe Asn Ile Leu
        915                 920                 925 aag aga agt ttt agt gct tca gga gga gaa aga caa tcc caa aca agg    2832
Lys Arg Ser Phe Ser Ala Ser Gly Gly Glu Arg Gln Ser Gln Thr Arg
    930                 935                 940 gac ttc act gga gga aca gga tca aga cca aga cca gca tca gca gga    2880
Asp Phe Thr Gly Gly Thr Gly Ser Arg Pro Arg Pro Ala Ser Ala Gly
945                 950                 955                 960 att gct gtg tcc cag agg aaa gtg cgt cag atc agt gat cct att cag    2928
Ile Ala Val Ser Gln Arg Lys Val Arg Gln Ile Ser Asp Pro Ile Gln
                965                 970                 975 cag ata tta att cag ctg cac aaa ata atc tat atc aca cag ctt cct    2976
Gln Ile Leu Ile Gln Leu His Lys Ile Ile Tyr Ile Thr Gln Leu Pro
            980                 985                 990 cca gct ttg cac cac aat ttg aaa aga agg gtt ata gag aga ttc aag    3024
Pro Ala Leu His His Asn Leu Lys Arg Arg Val Ile Glu Arg Phe Lys
        995                 1000                1005 aaa tcc ctc ttc agc cag cag agt aac cct tgt aat ttg aaa tct gaa    3072
Lys Ser Leu Phe Ser Gln Gln Ser Asn Pro Cys Asn Leu Lys Ser Glu
    1010                1015                1020 att aaa aag tta tct cag gga tct cca gaa ccg att gag ccc aac ttt    3120
Ile Lys Lys Leu Ser Gln Gly Ser Pro Glu Pro Ile Glu Pro Asn Phe
1025                1030                1035                1040 ttc aca gca gat tac cat tta tta cat cgt tca tcc ggt gga aac agc    3168
Phe Thr Ala Asp Tyr His Leu Leu His Arg Ser Ser Gly Gly Asn Ser
                1045                1050                1055 ctg tcc cca aat gac cct aca ggt tta cca acc agc att gaa ttg gag    3216
Leu Ser Pro Asn Asp Pro Thr Gly Leu Pro Thr Ser Ile Glu Leu Glu
            1060                1065                1070 gaa gga ata aca tat gaa cag atg cag act gtg att gaa gaa gtc ctt    3264
Glu Gly Ile Thr Tyr Glu Gln Met Gln Thr Val Ile Glu Glu Val Leu
        1075                1080                1085 gag gaa agt ggc tat tac aat ttt aca tct aac agg tat cat tcc tat    3312
Glu Glu Ser Gly Tyr Tyr Asn Phe Thr Ser Asn Arg Tyr His Ser Tyr
    1090                1095                1100 cca tgg ggg acc aag aat cac cca acc aaa aga tga                    3348
Pro Trp Gly Thr Lys Asn His Pro Thr Lys Arg *
1105                1110                1115

<210> SEQ ID NO 4
<211> LENGTH: 266
<212> TYPE: PRT
<213> ORGANISM: Artificial Sequence
<220> FEATURE:
<223> OTHER INFORMATION: consensus

<400> SEQUENCE: 4

Leu Gly Glu Gly Ser Phe Gly Lys Val Tyr Lys Ala Lys His Lys Thr
 1               5                  10                  15

Gly Lys Ile Val Ala Val Lys Ile Leu Lys Lys Glu Ser Leu Ser Leu
            20                  25                  30

Arg Glu Ile Gln Ile Leu Lys Arg Leu Ser His Pro Asn Ile Val Arg
```

```
                35                  40                  45
Leu Leu Gly Val Phe Glu Asp Thr Asp His Leu Tyr Leu Val Met
    50                  55                  60
Glu Tyr Met Glu Gly Gly Asp Leu Phe Asp Tyr Leu Arg Arg Asn Gly
65                  70                  75                  80
Pro Leu Ser Glu Lys Glu Ala Lys Lys Ile Ala Leu Gln Ile Leu Arg
                85                  90                  95
Gly Leu Glu Tyr Leu His Ser Asn Gly Ile Val His Arg Asp Leu Lys
                100                 105                 110
Pro Glu Asn Ile Leu Leu Asp Glu Asn Gly Thr Val Lys Ile Ala Asp
                115                 120                 125
Phe Gly Leu Ala Arg Leu Leu Glu Lys Leu Thr Thr Phe Val Gly Thr
            130                 135                 140
Pro Trp Tyr Met Met Ala Pro Glu Val Ile Leu Gly Arg Gly Tyr
145                 150                 155                 160
Ser Ser Lys Val Asp Val Trp Ser Leu Gly Val Ile Leu Tyr Glu Leu
                165                 170                 175
Leu Thr Gly Gly Pro Leu Phe Pro Gly Ala Asp Leu Pro Ala Phe Thr
            180                 185                 190
Gly Gly Asp Glu Val Asp Gln Leu Ile Ile Phe Val Leu Lys Leu Pro
        195                 200                 205
Phe Ser Asp Glu Leu Pro Lys Thr Arg Ile Asp Pro Leu Glu Glu Leu
    210                 215                 220
Phe Arg Ile Lys Lys Arg Arg Leu Pro Leu Pro Ser Asn Cys Ser Glu
225                 230                 235                 240
Glu Leu Lys Asp Leu Leu Lys Lys Cys Leu Asn Lys Asp Pro Ser Lys
                245                 250                 255
Arg Pro Gly Ser Ala Thr Ala Lys Glu Ile
                260                 265

<210> SEQ ID NO 5
<211> LENGTH: 40
<212> TYPE: PRT
<213> ORGANISM: Artificial Sequence
<220> FEATURE:
<223> OTHER INFORMATION: consensus

<400> SEQUENCE: 5

Asn Pro Glu Asn Lys Gln Ala Val Val Glu Ala Gly Ala Leu Pro Pro
1               5                   10                  15
Leu Val Gln Leu Leu Ser Pro Asp Glu Val Gln Glu Glu Ala Ala
            20                  25                  30
Trp Ala Leu Ser Asn Leu Ala Ala
        35                  40

<210> SEQ ID NO 6
<211> LENGTH: 34
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 1
<223> OTHER INFORMATION: The amino acid residue at position 1 can be
      leu, Ile, or Val.
<220> FEATURE:
<221> NAME/KEY: VARIANT
<222> LOCATION: 3,5
<223> OTHER INFORMATION: The amino acid residue at positions 3 and 5 can
```

```
        be any amino acid except Pro.
<220> FEATURE:
<221> NAME/KEY: VARIANT
<222> LOCATION: 6
<223> OTHER INFORMATION: The amino acid residue at position 6 can be
      Phe, Tyr, Trp, Met, Gly, Ser, Thr, Asn, or His.
<220> FEATURE:
<221> NAME/KEY: VARIANT
<222> LOCATION: 7
<223> OTHER INFORMATION: The amino acid residue at position 7 can be
      Ser, Gly or Ala.
<220> FEATURE:
<221> NAME/KEY: VARIANT
<222> LOCATION: 8
<223> OTHER INFORMATION: The amino acid residue at position 8 can be any
      amino acid except Pro or Trp.
<220> FEATURE:
<221> NAME/KEY: VARIANT
<222> LOCATION: 9
<223> OTHER INFORMATION: The amino acid residue at position 9 can be
      Leu, Ile, Val, Cys, Ala, or Thr.
<220> FEATURE:
<221> NAME/KEY: VARIANT
<222> LOCATION: 10
<223> OTHER INFORMATION: The amino acid residue at position 10 can be
      any amino acid except Pro or Asp.
<220> FEATURE:
<221> NAME/KEY: VARIANT
<222> LOCATION: 11
<223> OTHER INFORMATION: The amino acid residue at position 11 can be
      any amino acid.
<220> FEATURE:
<221> NAME/KEY: VARIANT
<222> LOCATION: 12
<223> OTHER INFORMATION: The amino acid residue at position 12 can be
      Gly, Ser, Thr, Ala, Cys, Leu, Ile, Val, Met, Phe, or Tyr.
<220> FEATURE:
<221> NAME/KEY: VARIANT
<222> LOCATION: (13)...(30)
<223> OTHER INFORMATION: This segment can be between 5 and 18 amino
      acids in length.  The amino acid residues at these
      positions can be any amino acid.
<220> FEATURE:
<221> NAME/KEY: VARIANT
<222> LOCATION: 31
<223> OTHER INFORMATION: The amino acid residue at position 31 can be
      Leu, Ile, Val, Met, Phe, Tyr, Trp, Cys, Ser, Thr, Ala, or Arg.
<220> FEATURE:
<221> NAME/KEY: VARIANT
<222> LOCATION: 32
<223> OTHER INFORMATION: The amino acid residue at position 32 can be
      Ala, Ile, Val, or Pro.
<220> FEATURE:
<221> NAME/KEY: VARIANT
<222> LOCATION: 33
<223> OTHER INFORMATION: The amino acid residue at position 33 can be
      Leu, Ile, Val, Met, Phe, Ala, Gly, Cys, Lys, or Arg.

<400> SEQUENCE: 6

Xaa Gly Xaa Gly Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Lys

<210> SEQ ID NO 7
<211> LENGTH: 13
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 1,11,12,13
<223> OTHER INFORMATION: The amino acid residue at positions 1, 11, 12,
``` or 13 can be Leu, Ile, Val, Met, Phe, Tyr, or Cys.
<220> FEATURE:
<221> NAME/KEY: VARIANT
<222> LOCATION: 2,4,8,9
<223> OTHER INFORMATION: The amino acid residue at positions 2, 4, 8, or
     9 can be any amino acid.
<220> FEATURE:
<221> NAME/KEY: VARIANT
<222> LOCATION: 3
<223> OTHER INFORMATION: The amino acid residue at position 3 can be His
     or Tyr.
<220> FEATURE:
<221> NAME/KEY: VARIANT
<222> LOCATION: 6
<223> OTHER INFORMATION: The amino acid residue at position 6 can be
     Leu, Ile, Val, Met, Phe or Tyr.
<220> FEATURE:
<221> NAME/KEY: VARIANT
<222> LOCATION: 7
<223> OTHER INFORMATION: The amino acid residue at position 7 can be
     Arg, Ser, Thr, Ala or Cys.

<400> SEQUENCE: 7

Xaa Xaa Xaa Xaa Asp Xaa Xaa Xaa Asn Xaa Xaa Xaa
 1               5                  10

<210> SEQ ID NO 8
<211> LENGTH: 9
<212> TYPE: PRT
<213> ORGANISM: Artificial Sequence
<220> FEATURE:
<223> OTHER INFORMATION: consensus
<220> FEATURE:
<221> NAME/KEY: VARIANT
<222> LOCATION: 1
<223> OTHER INFORMATION: The amino acid residue at position 1 can be Arg
     or Lys.
<220> FEATURE:
<221> NAME/KEY: VARIANT
<222> LOCATION: 2
<223> OTHER INFORMATION: The amino acid residue at position 2 can be Leu
     or Ile.
<220> FEATURE:
<221> NAME/KEY: VARIANT
<222> LOCATION: (3)...(7)
<223> OTHER INFORMATION: The amino acid residue at positions 3 through 7
     can be any amino acid.
<220> FEATURE:
<221> NAME/KEY: VARIANT
<222> LOCATION: 8
<223> OTHER INFORMATION: The amino acid residue at position 8 can be His
     or Gln.

<400> SEQUENCE: 8

Xaa Xaa Xaa Xaa Xaa Xaa Xaa Xaa Leu
 1               5

<210> SEQ ID NO 9
<211> LENGTH: 854
<212> TYPE: PRT
<213> ORGANISM: Homo sapiens

<400> SEQUENCE: 9

Met Arg Val Leu Phe Asp Glu Ser Val Leu Pro Pro Thr Val Tyr Phe
 1               5                  10                  15

Lys Asn Cys Ser Ile Leu Phe Leu Ala Ser Leu Cys Ala Phe Gly Val
                20                  25                  30

Leu Thr Gly Leu Leu Val Trp Ser Phe Met Gln Tyr Met Glu Ile Val
         35                  40                  45

Ala Asn Glu Tyr Leu Gly Tyr Gly Glu Glu Gln His Thr Val Asp Lys
     50                  55                  60

```
Leu Val Asn Met Thr Tyr Ile Phe Gln Lys Leu Ala Val Lys Asp
 65                  70                  75                  80

Gln Arg Glu Trp Val Thr Thr Ser Gly Ala His Lys Thr Leu Val Asn
             85                  90                  95

Leu Leu Gly Ala Arg Asp Thr Asn Val Leu Leu Gly Ser Leu Leu Ala
             100                 105                 110

Leu Ala Ser Leu Ala Glu Arg Leu Thr Ala Glu Leu Leu Arg Leu Leu
             115                 120                 125

Cys Ala Glu Pro Gln Val Lys Glu Gln Val Lys Leu Tyr Glu Gly Ile
130                 135                 140

Pro Val Leu Leu Ser Leu Leu His Ser Asp His Leu Lys Leu Leu Trp
145                 150                 155                 160

Ser Ile Val Trp Ile Leu Val Gln Val Cys Glu Asp Pro Glu Thr Ser
             165                 170                 175

Val Glu Ile Arg Ile Trp Gly Gly Ile Lys Gln Leu Leu His Ile Leu
             180                 185                 190

Gln Gly Asp Arg Asn Phe Val Ser Asp His Ser Ser Ile Gly Ser Leu
             195                 200                 205

Ser Ser Ala Asn Ala Ala Gly Arg Ile Gln Gln Leu His Leu Ser Glu
210                 215                 220

Asp Leu Ser Pro Arg Glu Ile Gln Glu Asn Thr Phe Ser Leu Gln Ala
225                 230                 235                 240

Ala Cys Cys Ala Ala Leu Thr Glu Leu Val Leu Asn Asp Thr Asn Ala
             245                 250                 255

His Gln Val Val Gln Glu Asn Gly Val Tyr Thr Ile Ala Lys Leu Ile
             260                 265                 270

Leu Pro Asn Lys Gln Lys Asn Ala Ala Lys Ser Asn Leu Leu Gln Cys
             275                 280                 285

Tyr Ala Phe Arg Ala Leu Arg Phe Leu Phe Ser Met Glu Arg Asn Arg
290                 295                 300

Pro Leu Phe Lys Arg Leu Phe Pro Thr Asp Leu Phe Glu Ile Phe Ile
305                 310                 315                 320

Asp Ile Gly His Tyr Val Arg Asp Ile Ser Ala Tyr Glu Glu Leu Val
             325                 330                 335

Ser Lys Leu Asn Leu Leu Val Glu Asp Glu Leu Lys Gln Ile Ala Glu
             340                 345                 350

Asn Ile Glu Ser Ile Asn Gln Asn Lys Ala Pro Leu Lys Tyr Ile Gly
             355                 360                 365

Asn Tyr Ala Ile Leu Asp His Leu Gly Ser Gly Ala Phe Gly Cys Val
370                 375                 380

Tyr Lys Val Arg Lys His Ser Gly Gln Asn Leu Leu Ala Met Lys Glu
385                 390                 395                 400

Val Asn Leu His Asn Pro Ala Phe Gly Lys Asp Lys Asp Arg Asp
             405                 410                 415

Ser Ser Val Arg Asn Ile Val Ser Glu Leu Thr Ile Ile Lys Glu Gln
             420                 425                 430

Leu Tyr His Pro Asn Ile Val Arg Tyr Tyr Lys Thr Phe Leu Glu Asn
             435                 440                 445

Asp Arg Leu Tyr Ile Val Met Glu Leu Ile Glu Gly Ala Pro Leu Gly
450                 455                 460

Glu His Phe Ser Ser Leu Lys Glu Lys His His His Phe Thr Glu Glu
465                 470                 475                 480
```

```
Arg Leu Trp Lys Ile Phe Ile Gln Leu Cys Leu Ala Leu Arg Tyr Leu
                485                 490                 495
His Lys Glu Lys Arg Ile Val His Arg Asp Gln Thr Pro Asn Asn Ile
                500                 505                 510
Met Leu Gly Asp Lys Asp Lys Val Thr Val Thr Asp Phe Gly Leu Ala
                515                 520                 525
Lys Gln Lys Gln Glu Asn Ser Lys Leu Thr Ser Val Val Gly Thr Ile
530                 535                 540
Leu Tyr Ser Cys Pro Glu Val Leu Lys Ser Glu Pro Tyr Gly Glu Lys
545                 550                 555                 560
Ala Asp Val Trp Ala Val Gly Cys Ile Leu Tyr Gln Met Ala Thr Leu
                565                 570                 575
Ser Pro Pro Phe Tyr Ser Thr Asn Met Leu Ser Leu Ala Thr Lys Ile
                580                 585                 590
Val Glu Ala Val Tyr Glu Pro Val Pro Glu Gly Ile Tyr Ser Glu Lys
                595                 600                 605
Val Thr Asp Thr Ile Ser Arg Cys Leu Thr Pro Asp Ala Glu Ala Arg
                610                 615                 620
Pro Asp Ile Val Glu Val Ser Ser Met Ile Ser Asp Val Met Met Lys
625                 630                 635                 640
Tyr Leu Asp Asn Leu Ser Thr Ser Gln Leu Ser Leu Glu Lys Lys Leu
                645                 650                 655
Glu Arg Glu Arg Arg Arg Thr Gln Arg Tyr Phe Met Glu Ala Asn Arg
                660                 665                 670
Asn Thr Val Thr Cys His His Glu Leu Ala Val Leu Ser His Glu Thr
                675                 680                 685
Phe Glu Lys Ala Ser Leu Ser Ser Ser Ser Gly Ala Ala Ser Leu
                690                 695                 700
Lys Ser Glu Leu Ser Glu Ser Ala Asp Leu Pro Pro Glu Gly Phe Gln
705                 710                 715                 720
Ala Ser Tyr Gly Lys Asp Glu Asp Arg Ala Cys Asn Glu Ile Leu Ser
                725                 730                 735
Asp Asp Asn Phe Asn Leu Glu Asn Ala Glu Lys Asp Thr Tyr Ser Glu
                740                 745                 750
Val Asp Asp Glu Leu Asp Ile Ser Asp Asn Ser Ser Ser Ser Ser Ser
                755                 760                 765
Ser Pro Leu Lys Glu Ser Thr Phe Asn Ile Leu Lys Arg Ser Phe Ser
770                 775                 780
Ala Ser Gly Gly Glu Arg Gln Ser Gln Thr Arg Asp Phe Thr Gly Gly
785                 790                 795                 800
Thr Gly Ser Arg Pro Arg Pro Gly Pro Gln Met Gly Thr Phe Leu Trp
                805                 810                 815
Gln Ala Ser Ala Gly Ile Ala Val Ser Gln Arg Lys Val Arg Gln Ile
                820                 825                 830
Ser Asp Pro Ile Gln Gln Ile Leu Ile Gln Leu His Lys Ile Ile Tyr
                835                 840                 845
Ile Thr Gln Leu Pro Pro
       850
```

<210> SEQ ID NO 10
<211> LENGTH: 23
<212> TYPE: DNA
<213> ORGANISM: Artificial Sequence
<220> FEATURE:
<223> OTHER INFORMATION: primer -continued

```
<400> SEQUENCE: 10
aagactgggc tgagtttgtg aag                                          23

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ccaagggatt gcctacaaac a                                            21

<210> SEQ ID NO 12
<211> LENGTH: 24
<212> TYPE: DNA
<213> ORGANISM: Artificial Sequence
<220> FEATURE:
<223> OTHER INFORMATION: probe

<400> SEQUENCE: 12
aactgccatg cctcgaagac ctgg                                         24
```

14815, A HUMAN KINASE FAMILY MEMBER AND USES THEREFOR

CROSS-REFERENCES TO RELATED APPLICATION

The application claims priority to U.S. Provisional Application No. 60/345,853, filed Jan. 2, 2002, now abandoned.

BACKGROUND OF THE INVENTION

The tight association of phosphate with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) *Science* 250:786–791; Birchmeier et al. (1993) *Bioessays* 15:185–189). For example, these kinases have been shown to participate in the transmission of signals from growth-factor receptors (Sturgill et al. (1988) *Nature* 344:715–718; Gomez et al. (1991) *Nature* 353:170–173), control of entry of cells into mitosis (Nurse (1990) *Nature* 344:503–508; Mailer (1991) *Curr. Opin. Cell Biol.* 3:269–275), and regulation of actin bundling (Husain-Chishti et al. (1988) *Nature* 334:718–721). Protein kinases serve as growth factor receptors and signal transducers and have been implicated in cellular transformation and malignancy (Hunter et al. (1992) *Cell* 70:375–387; Posada et al. (1992) *Mol. Biol. Cell* 3:583–592; Hunter et al. (1994) *Cell* 79:573–582). Alterations in kinase genes and their products can lead to deregulated cell proliferation, a hallmark of cancer. Modulation of these genes and their regulatory activities may permit the control of tumor cell proliferation and invasion.

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks et al. (1988) *Science* 241:42–52).

SUMMARY OF THE INVENTION

The present invention is based, in part, on the discovery of a novel kinase family member, referred to herein as "14815". The kinase molecule of the invention shares characteristics with members of the tyrosine kinase family. The nucleotide sequence of a cDNA encoding 14815 is shown in SEQ ID NO:1, and the amino acid sequence of a 14815 polypeptide is shown in SEQ ID NO:2. In addition, the nucleotide sequence of the coding region is depicted in SEQ ID NO:3.

Accordingly, in one aspect, the invention features a nucleic acid molecule which encodes a 14815 protein or polypeptide, e.g., a biologically active portion of the 14815 protein. In a preferred embodiment, the isolated nucleic acid molecule encodes a polypeptide having the amino acid sequence of SEQ ID NO:2. In other embodiments, the invention provides isolated 14815 nucleic acid molecules having the nucleotide sequence shown in SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1 or SEQ ID NO:3. In other embodiments, the invention provides a nucleic acid molecule which hybridizes under a stringent hybridization condition as described herein to a nucleic acid molecule comprising the nucleotide sequence of SEQ ID NO: 1 or SEQ ID NO:3, wherein the nucleic acid encodes a full length 14815 protein or an active fragment thereof.

In a related aspect, the invention further provides nucleic acid constructs which include a 14815 nucleic acid molecule described herein. In certain embodiments, the nucleic acid molecules of the invention are operatively linked to native or heterologous regulatory sequences. Also included are vectors and host cells containing the 14815 nucleic acid molecules of the invention e.g., vectors and host cells suitable for producing polypeptides.

In another related aspect, the invention provides nucleic acid fragments suitable as primers or hybridization probes for the detection of 14815-encoding nucleic acids.

In still another related aspect, isolated nucleic acid molecules that are antisense to a 14815 encoding nucleic acid molecule are provided.

In another aspect, the invention features 14815 polypeptides, and biologically active or antigenic fragments thereof that are useful, e.g., as reagents or targets in assays applicable to treatment and diagnosis of kinase-associated or other 14815-associated disorders. In another embodiment, the invention provides 14815 polypeptides having a 14815 activity. Preferred polypeptides are 14815 proteins including at least one protein kinase domain, at least one, two, three, preferably four armadillo/beta-catenin-like repeat domains, and, preferably, having a 14815 activity, e.g., a 14815 activity as described herein.

In other embodiments, the invention provides 14815 polypeptides, e.g., a 14815 polypeptide having the amino acid sequence shown in SEQ ID NO:2; an amino acid sequence that is substantially identical to the amino acid sequence shown in SEQ ID NO:2; or an amino acid sequence encoded by a acid nucleic molecule having a nucleotide sequence which hybridizes under a stringent hybridization condition as described herein to a nucleic acid molecule comprising the nucleotide sequence of SEQ ID NO:1 or SEQ ID NO:3, wherein the nucleic acid encodes a full length 14815 protein or an active fragment thereof.

In a related aspect, the invention further provides nucleic acid constructs which include a 14815 nucleic acid molecule described herein.

In a related aspect, the invention provides 14815 polypeptides or fragments operatively linked to non-14815 polypeptides to form fusion proteins.

In another aspect, the invention features antibodies and antigen-binding fragments thereof, that react with, or more preferably specifically or selectively bind 14815 polypeptides.

In another aspect, the invention provides methods of screening for compounds that modulate the expression or activity of the 14815 polypeptides or nucleic acids.

In still another aspect, the invention provides a process for modulating 14815 polypeptide or nucleic acid expression or activity, e.g., using the compounds identified in the screens described herein. In certain embodiments, the methods involve treatment of conditions related to aberrant activity or expression of the 14815 polypeptides or nucleic acids, such as conditions or disorders involving aberrant or deficient kinase function or expression. Examples of such disorders include, but are not limited to, cellular proliferative and/or differentiative disorders, neurological disorders, inflammatory disorders, liver disorders, apoptotic disorders, metabolic disorders and hormonal disorders.

The invention also provides assays for determining the activity of or the presence or absence of 14815 polypeptides or nucleic acid molecules in a biological sample, including for disease diagnosis.

In a further aspect, the invention provides assays for determining the presence or absence of a genetic alteration in a 14815 polypeptide or nucleic acid molecule, including for disease diagnosis.

In another aspect, the invention features a two dimensional array having a plurality of addresses, each address of the plurality being positionally distinguishable from each other address of the plurality, and each address of the plurality having a unique capture probe, e.g., a nucleic acid or peptide sequence. At least one address of the plurality has a capture probe that recognizes a 14815 molecule. In one embodiment, the capture probe is a nucleic acid, e.g., a probe complementary to a 14815 nucleic acid sequence. In another embodiment, the capture probe is a polypeptide, e.g., an antibody specific for 14815 polypeptides. Also featured is a method of analyzing a sample by contacting the sample to the aforementioned array and detecting binding of the sample to the array.

Other features and advantages of the invention will be apparent from the following detailed description, and from the claims.

DETAILED DESCRIPTION OF THE INVENTION

Figure 1:
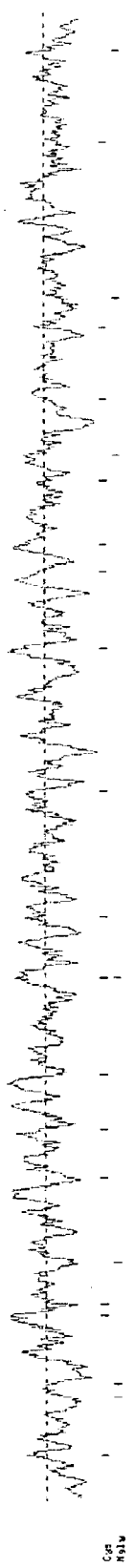
FIG. 1 depicts a hydropathy plot of human 14815. Relatively hydrophobic residues are shown above the dashed horizontal line, and relatively hydrophilic residues are below the dashed horizontal line. The cysteine residues (cys) are indicated by short vertical lines just below the hydropathy trace. The numbers corresponding to the amino acid sequence of human 14815 are indicated. Polypeptides of the invention include fragments which include: all or part of a hydrophobic sequence, e.g., a sequence above the dashed line, e.g., the sequence from about amino acid 135 to 143, from about 225 to 237, and from about 634 to 642 of SEQ ID NO:2; all or part of a hydrophilic sequence, e.g., a sequence below the dashed line, e.g., the sequence from about amino acid 51 to 61, from about 90 to 104, and from about 802 to 815 of SEQ ID NO:2; a sequence which includes a Cys, or a glycosylation site.

The human 14815 sequence (SEQ ID NO:1), which is approximately 3919 nucleotides long including untranslated regions, contains a predicted methionine-initiated coding sequence of about 3348 nucleotides, including the termination codon (nucleotides indicated as coding of SEQ ID NO:1, SEQ ID NO:3). The coding sequence encodes a 1115 amino acid protein (SEQ ID NO:2).

Human 14815 contains the following regions or other structural features (for general information regarding PFAM identifiers, PS prefix and PF prefix domain identification numbers, refer to Sonnhammer et al. (1997) *Protein* 28:405–420 or the Pfam website maintained in several locations, e.g. by the Sanger Institute (pfam.sanger.ac.uk), Washington University (pfam.wustl.edu), the Karolinska Institute (pfam.cgr.kr.se) or Institut de la National Recherche Agronomique (pfam.jouy.inra.fr) and the ExPASy (Expert Protein Analysis System) proteomics server of the Swiss Institute of Bioinformatics (SIB), Geneva, Switzerland:

a protein kinase domain (PFAM Accession Number PF00069, SEQ ID NO:4) located at about amino acid residues 519 to 779 of SEQ ID NO:2;

four armadillo/beta-catenin-like repeat domains (PFAM Accession Number PF00514, SEQ ID NO:5) located at about amino acid residues 198 to 238, 239 to 279, 280 to 320, and 401 to 448 of SEQ ID NO:2;

one protein kinases ATP-binding region signature (Prosite PS00107, SEQ ID NO:6) located at about amino acids 525 to 548 of SEQ ID NO:2;

one tyrosine protein kinase active site signature (Prosite PS00109, SEQ ID NO:7) located at about amino acids 651 to 663 of SEQ ID NO:2;

one coiled coil structure (PSORT, Nakai and Kanehisa (1992) *Genomics* 14:897–911), see the PSORT website maintained by the Human Genome Center at the Institute of Medical Science in the University of Tokyo, psort.nibb.ac.jp.) located at about amino acids 472 to 500 of SEQ ID NO:2;

two $2^{nd}$ peroxisomal targeting signals (PTS2, SEQ ID NO:8, PSORT, Nakai and Kanehisa (1992) *Genomics* 14:897–911), see the PSORT website maintained by the Human Genome Center at the Institute of Medical Science in the University of Tokyo, psort.nibb.ac.jp.) located at about amino acids 329 to 337 and 630 to 638 of SEQ ID NO:2;

one vacuolar targeting motif (VAC, PSORT, Nakai and Kanehisa (1992) *Genomics* 14:897–911), see the PSORT website maintained by the Human Genome Center at the Institute of Medical Science in the University of Tokyo, psort.nibb.ac.jp.) located at about amino acids 421 to 424 of SEQ ID NO:2;

fourteen protein kinase C phosphorylation sites (Prosite PS00005) located at about amino acids 11 to 13, 15 to 17, 22 to 24, 40 to 42, 266 to 268, 376 to 378, 567 to 569, 618 to 620, 755 to 757, 812 to 814, 852 to 854, 964 to 966, 1098 to 1100, and 1113 to 1115 of SEQ ID NO:2;

fifteen casein kinase II phosphorylation sites (Prosite PS00006) located at about amino acids 22 to 25, 58 to 61, 235 to 238, 324 to 327, 376 to 379, 479 to 482, 593 to 596, 618 to 621, 670 to 673, 696 to 699, 898 to 901, 935 to 938, 1058 to 1061, 1067 to 1070, and 1082 to 1085 of SEQ ID NO:2;

four cAMP/cGMP-dependent protein kinase phosphorylation sites (Prosite PS00004) located at about amino acids 267 to 270, 537 to 540, 809 to 812, and 1026 to 1029 of SEQ ID NO:2;

seven N-glycosylation sites (Prosite PS00001) located at about amino acids 86 to 89, 96 to 99, 187 to 190, 401 to 404, 793 to 796, 911 to 914, and 1095 to 1098 of SEQ ID NO:2;

one tyrosine kinase phosphorylation site (Prosite PS00007) located at about amino acids 740 to 746 of SEQ ID NO:2; and eleven N-myristoylation sites (Prosite PS00008) located at about amino acids 67 to 72, 156 to 161, 209 to 214, 219 to 224, 228 to 233, 355 to 360, 528 to 533, 609 to 614, 948 to 953, 960 to 965, and 1064 to 1069 of SEQ ID NO:2.

A plasmid containing the nucleotide sequence encoding human 14815 can be named Fbh14815FL.

The 14815 protein contains a significant number of structural characteristics in common with members of the kinase family, in particular, the tyrosine protein kinase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologs of non-human origin, e.g., rat or mouse proteins. Members of a family also can have common functional characteristics.

As used herein, the term "kinase" includes a protein or polypeptide which is capable of modulating its own phosphorylation state or the phosphorylation state of another molecule, e.g., protein or polypeptide. Typically, a kinase obtains the phosphate group from a triphosphate molecule, e.g., a nucleotide (e.g., adenosine triphosphate (ATP)). Protein kinases can have a specificity for (i.e., a specificity to phosphorylate) serine or threonine residues, tyrosine residues, or serine, threonine and tyrosine residues, e.g., the dual specificity kinases. A kinase with specificity for tyrosine residues is referred to herein as a "tyrosine kinase."

Members of a kinase family of proteins can be cytoplasmic, membrane-bound, or extracellular, and have a catalytic domain to perform the phosphorylation function. Regulation of the kinase activity can occur by the association of the catalytic domain with another molecule, e.g. another protein, or by modification of the kinase domain to modulate the kinase enzymatic activity. A kinase also can have one or more additional domains to enable it to associate with a specific molecule or location. Such an association can contribute to the regulation of the kinase or the regulatory function of the kinase. Examples of serine/threonine protein kinases include, but are not limited to, cyclin-dependent kinases, protein kinase C (PKC), and casein kinase II. Examples of tyrosine protein kinases include, but are not limited to, members of the src subfamily, including some oncogenes, members of the c-src kinase subfamily, and members of the receptor tyrosine kinase subfamily, including growth factor, e.g. platelet-derived growth factor and vascular endothelial growth factor, and hormone, e.g. insulin receptors. The 14815 polypeptide is a tyrosine kinase homologous to a partial amino acid sequence of a kinase family member, SGK237 (SEQ ID NO:9, in WO 200166594). A GAP alignment of this amino acid sequence to the 14815 polypeptide of SEQ ID NO:2 found 95.4% identity between the two sequences in the 854 amino acid region of overlap (as calculated in matblas from the blosum50matrix).

A 14815 polypeptide can include a "protein kinase domain" or regions homologous with a "protein kinase domain". A 14815 polypeptide can further include an "armadillo/beta-catenin-like repeat domain" or regions homologous with an "armadillo/beta-catenin-like repeat domain."

As used herein, the term "protein kinase domain" includes an amino acid sequence of about 200 to 320 amino acid residues in length and having a bit score for the alignment of the sequence to the protein kinase domain (HMM) of at least 200. Preferably a protein kinase domain mediates catalysis of protein phosphorylation and can mediate the interaction with other domains, e.g. cyclin domains, kinase domains or ankyrin repeat domains. Preferably, a protein kinase domain includes at least about 220 to 300 amino acids, more preferably about 240 to 280 amino acid residues, or about 255 to 265 amino acids and has a bit score for the alignment of the sequence to the protein kinase domain (HMM) of at least 210, 220, 230 or greater.

The protein kinase domain can include a Prosite protein kinases ATP-binding signature sequence PS00107 (SEQ ID NO:6), or sequences homologous thereto at about amino acid residues 525 to 548 of SEQ ID NO:2. This sequence contains contains an active site lysine, e.g. K-548, which can bind the phosphate donor nucleotide, e.g., adenosine triphosphate. The protein kinase domain also can include a Prosite tyrosine protein kinases active site signature sequence PS00109 (SEQ ID NO:7), or sequences homologous thereto at about amino acid residues 651 to 663 of SEQ ID NO:2. Within this sequence is an active site aspartate residue, e.g. D-655.

As noted for the kinase signature sequence above, K-548 of SEQ ID NO:2 can be involved in ATP binding for the 14815 polypeptide. Experiments involving kinases typically use a kinase-dead mutant with a substitution of the binding site lysine, e.g. K-548, to a different amino acid residue, e.g. alanine by mutating nucleotides bases encoding the lysine, e.g. nucleotides 1824 and 1825 of SEQ ID NO:1 from adenine to guanine and cytosine, respectively, so the codon for amino acid residue 548 of SEQ ID NO:2 is GCG instead of the wild type AAG. The results of those experiments typically demonstrate loss of 14815 kinase activity with A instead of K at the binding site, e.g. residue 548 of SEQ ID NO:2. Thus, further embodiments of the invention are a substitution for K at residue 548 of SEQ ID NO:2, or a portion thereof, e.g. a polypeptide comprising a fragment of 14815, e.g. a polypeptide comprising the kinase domain, and nucleic acid sequences encoding the substitution. Similarly, for the tyrosine kinase signature sequence above, D-655 of SEQ ID NO:2 can be an active site residue for the 14815 polypeptide. Experiments involving kinases typically use a kinase-dead mutant with a substitution of the active site aspartate, e.g. D-655, to a different amino acid residue, e.g. alanine by mutating nucleotides bases encoding the lysine, e.g. nucleotides 2146 and 2147 of SEQ ID NO:1 from adenine and thymine to cytosine and guanine, respectively, so the codon for amino acid residue 655 of SEQ ID NO:2 is GCG instead of the wild type GAT. The results of those experiments typically demonstrate loss of 14815 kinase activity with A instead of D at the active site, e.g. residue 655 of SEQ ID NO:2. Thus, further embodiments of the invention are a substitution for D at residue 655 of SEQ ID NO:2, or a portion thereof, e.g. a polypeptide comprising a fragment of 14815, e.g. a polypeptide comprising the kinase domain, and nucleic acid sequences encoding the substitution.

The protein kinase domain (HMM) has been assigned the PFAM Accession Number PF00069 (SEQ ID NO:4, (see the Pfam website maintained in several locations, e.g. by the Sanger Institute (pfam.sanger.ac.uk), Washington University (pfam.wustl.edu), the Karolinska Institute (pfam.cgr.kr.se) or Institut de la National Recherche Agronomique (pfam.jouy.inra.fr)). The region containing the protein kinase domain (HMM) also has been assigned the SMART (modular architecture analysis) identifier "serine/threonine protein kinases, catalytic domain" (SM0220) and "tyrosine kinases, catalytic domain" (SM0219, smart.embl-heidelberg) and designated as located about amino acid residues 519 to 791 or 783, respectively, of SEQ ID NO:2. An alignment of the protein kinase domain (amino acids 519 to 779 of SEQ ID NO:2) of human 14815 proteins with the Pfam protein kinase domain consensus amino acid sequence (SEQ ID NO:4) derived from a hidden Markov model yields a bit score of 236.7.

In a preferred embodiment, a 14815 polypeptide or protein has a "protein kinase domain" or a region which includes at least about 220 to 300 amino acids, more preferably about 240 to 280 amino acid residues, or about 255 to 265 amino acid residues and has at least about 60%, 70% 80% 90% 95%, 99%, or 100% homology with a "protein kinase domain," e.g., the protein kinase domain of human 14815 (e.g., residues 519 to 779 of SEQ ID NO:2).

As used herein, the term "armadillo/beta-catenin-like repeat domain" includes an amino acid sequence of about 20 to 60 amino acid residues in length and having a bit score for the alignment of the sequence to the protein kinase domain (HMM) of at least 0.4. The armadillo/beta-catenin-like repeat domains typically have three alpha helices and the repeats can associate in a manner in which they form a super-helix. Preferably, armadillo/beta-catenin-like repeat domains mediate the interaction with another domain, e.g. a nucleoplasmin domain, an importin beta binding domain, a ras domain or a vinculin domain. These domains are found in proteins with diverse functions and locations, from activities in the nucleus, cytoplasm (or both, depending on the attachment of protein-modifying functional groups) and in cytoplasmic-membrane anchoring structures. The structure of the super-helix can create a groove with a particular charge characteristic to mediate the association of the proteins containing the respective domains. Preferably, an armadillo/beta-catenin-like repeat domain includes at least about 25 to 55 amino acids, more preferably about 30 to 50 amino acid residues, or about 35 to 45 amino acids and has a bit score for the alignment of the sequence to the protein kinase domain (HMM) of at least 0.6, 0.8, 1.0 or greater.

The armadillo/beta-catenin-like repeat domain (HMM) has been assigned the PFAM Accession Number PF00514 (SEQ ID NO:5, (see the Pfam website maintained in several locations, e.g. by the Sanger Institute (pfam.sanger.ac.uk), Washington University (pfam.wustl.edu), the Karolinska Institute (pfam.cgr.kr.se) or Institut de la National Recherche Agronomique (pfam.jouy.inra.fr)). The region containing the protein kinase domain (HMM) also has been assigned the SMART (modular architecture analysis) identifier "armadillo/beta-catenin-like repeats" (SM0185, smart.embl-heidelberg) and designated as located about amino acid residues 197 to 238, 278 to 320, and 401 to 448, of SEQ ID NO:2. Alignments of the armadillo/beta-catenin-like repeat domains (amino acids 198 to 238, 239 to 279, 280 to 320, and 401 to 448 of SEQ ID NO:2) of human 14815 proteins with the Pfam armadillo/beta-catenin-like repeat domain consensus amino acid sequence (SEQ ID NO:5) derived from a hidden Markov model yield bit scores of 15.5, 5.0, 6.3, and 1.1.

In a preferred embodiment, a 14815 polypeptide or protein has an "armadillo/beta-catenin-like repeat domain" or regions which include at least about 25 to 55 amino acids, more preferably about 30 to 50 amino acid residues, or about 35 to 45 amino acid residues and have at least about 60%, 70% 80% 90% 95%, 99%, or 100% homology with an "armadillo/beta-catenin-like repeat domain," e.g., the armadillo/beta-catenin-like repeat domains of human 14815 (e.g., residues 198 to 238, 239 to 279, 280 to 320, and 401 to 448 of SEQ ID NO:2).

To identify the presence of a "protein kinase" domain or an "armadillo/beta-catenin-like repeat" domain in a 14815 protein sequence, and make the determination that a polypeptide or protein of interest has a particular profile, the amino acid sequence of the protein can be searched against the Pfam database of HMMs (e.g., the Pfam database, release 2.1) using the default parameters (see the Pfam website maintained in several locations, e.g. by the Sanger Institute (pfam.sanger.ac.uk/Software/Pfam/HMM_search)). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) Proteins 28:405–420 and a detailed description of HMMs can be found, for example, in Gribskov et al. (1990) Meth. Enzymol. 183:146–159; Gribskov et al. (1987) Proc. Natl. Acad. Sci. USA 84:4355–4358; Krogh et al. (1994) J. Mol. Biol. 235:1501–1531; and Stultz et al. (1993) Protein Sci. 2:305–314, the contents of which are incorporated herein by reference. A search was performed against the HMM database resulting in the identification of a "protein kinase domain" domain in the amino acid sequence of human 14815 at about residues 519 to 779 of SEQ ID NO:2 and four "armadillo/beta-catenin-like repeat domains" at about residues 198 to 238, 239 to 279, 280 to 320, and 401 to 448 of SEQ ID NO:2.

An additional method to identify the presence of a "protein kinase" or an "armadillo/beta-catenin-like repeat" domain in a 14815 protein sequence, and make the determination that a polypeptide or protein of interest has a particular profile, the amino acid sequence of the protein can be searched against a SMART database (Simple Modular Architecture Research Tool, smart.embl-heidelberg) of HMMs as described in Schultz et al. (1998), Proc. Natl. Acad. Sci. USA 95:5857 and Schultz et al. (2000) Nucl. Acids Res 28:231. The database contains domains identified by profiling with the hidden Markov models of the HMMer2 search program (Durbin et al. (1998) Biological sequence analysis: probabilistic models of proteins and nucleic acids. Cambridge University Press; see HMMer2 program documentation maintained by the Washington University in St. Louis Mo., hmmer.wustl.edu/). The database also is extensively annotated and monitored by experts to enhance accuracy. A search was performed against the HMM database resulting in the identification of a "serine/threonine protein kinases, catalytic domain" in the amino acid sequence of human 14815 at about residues 519 to 791 of SEQ ID NO:2, a "tyrosine kinases, catalytic domain" in the amino acid sequence of human 14815 at about residues 519 to 783 of SEQ ID NO:2 and three "armadillo/beta-catenin-like repeats" in the amino acid sequence of human 14815 at about residues 197 to 238, 278 to 320, and 401 to 448, of SEQ ID NO:2.

A human 14815 protein also can include a coiled coil structure (PSORT, Nakai and Kanehisa (1992) Genomics 14:897–911). Coiled coil structures are supercoiled helical domains responsible for the oligomerization of proteins. There is a characteristic heptad repeat (h-x-x-h-x-x-x)n in the coiled coil structures, where h represents hydrophobic residues (Beck and Brodsky (1998) J. Struct. Biol. 122:17–29). Coiled coil structures are found in a wide variety of proteins, including cytoskeletal, nuclear, muscle, cell surface, extracellular, plasma, bacterial, and viral proteins and can be found in the 14815 polypeptide at about amino acids 472 to 500 of SEQ ID NO:2.

A human 14815 protein can further include at least one, preferably two 2$^{nd}$ peroxisomal targeting signals (PTS2, SEQ ID NO:8, PSORT, Nakai and Kanehisa (1992) *Genomics* 14:897–911). Peroxisomes are membrane-bound organelles containing enzymes which perform a number of functions, metabolic, catabolic and synthetic. Examples of functions at least partially performed by peroxisomal enzymes include, but are not limited to fatty acid metabolism, oxygen radical clearance and cholesterol synthesis. Peroxisomes are most abundant in liver, but many disorders of peroxisomes are manifested as metabolic diseases or neurological diseases. The prediction of the peroxisome signal was accompanied by the secondary, seemingly conflicting predictions of a mitochondrial presequence cleavage site, an endoplasmic reticulum membrane retention signal and a vacuolar targeting motif (VAC) by PSORT. Taken together, these results suggest that the 14815 kinase can have an intracellular location of a membrane-bound organelle, e.g. a peroxisome, the endoplasmic reticulum, a mitochondrion, or a vacuole. Preferably, the 14815 kinase has an intracellular location of a peroxisome.

A 14815 family member can include at least one protein kinase domain; and at least one, two, three preferably four armadillo/beta-catenin-like repeat domains. A 14815 family member can include at least one protein kinases ATP-binding region signature (Prosite PS00107), at least one tyrosine protein kinase active site signature (Prosite PS00109), at least one coiled coil structure (PSORT coiled coil), and at least one, preferably two 2$^{nd}$ peroxisomal targeting signals (PSORT, PTS2). Furthermore, a 14815 family member can include at least one, two, three, four, five, six, seven, eight, nine, ten, eleven, twelve, thirteen, preferably fourteen protein kinase C phosphorylation sites (Prosite PS00005); at least one, two, three, four, five, six, seven, eight, nine, ten, eleven, twelve, thirteen, fourteen, preferably fifteen casein kinase II phosphorylation sites (Prosite PS00006); at least one, two, three, four, five, six, preferably seven N-glycosylation sites (Prosite PS00001); at least one, two, three, preferably four cAMP/cGMP protein kinase phosphorylation sites (Prosite PS00004); at least one tyrosine kinase phosphorylation site (Prosite PS00007); and at least one, two, three, four, five, six, seven, eight, nine, ten preferably eleven N-myristoylation sites (Prosite PS00008).

As the 14815 polypeptides of the invention can modulate 14815-mediated activities, they can be useful for developing novel diagnostic and therapeutic agents for kinase-associated or other 14815-associated disorders, as described below.

As used herein, a "kinase-associated activity" includes an activity which involves phosphorylation of a protein, e.g. phosphorylation of a serine or threonine residue on a protein. Protein kinases can play a role in signalling pathways associated with cellular growth. For example, protein kinases are involved in the regulation of signal transmission from cellular receptors, e.g., growth-factor receptors; entry of cells into mitosis; and the regulation of cytoskeleton function, e.g., actin bundling. These kinases can function in these biological activities because of their ability to phosphorylate themselves or other substrate molecules. Members of the kinase family can play a role in cyclin-dependent kinase-neurodegenerative diseases (Smith et al. (2001) *Cell Growth Differ.* 12:277–83), myotonic dystrophy (Ueda et al. (2000) *Prog. Histochem. Cytochem.* 35:187–251), and Peutz-Jeghers syndrome (Westerman and Wilson (1999) *Scand. J. Gastroenterol. Suppl.* 230:64–70).

As used herein, a "14815 activity", "biological activity of 14815" or "functional activity of 14815", refers to an activity exerted by a 14815 protein, polypeptide or nucleic acid molecule on e.g., a 14815-responsive cell or on a 14815 substrate, e.g., a protein substrate, as determined in vivo or in vitro. In one embodiment, a 14815 activity is a direct activity, such as an association with a 14815 target molecule. A "target molecule" or "binding partner" is a molecule with which a 14815 protein binds or interacts in nature. In an exemplary embodiment, 14815 is a kinase, e.g., a tyrosine protein kinase, and thus binds to or interacts in nature with a molecule, e.g., a nucleotide (e.g. adenosine triphosphate) and a protein substrate, e.g. a tyrosine-containing protein.

A 14815 activity can also be an indirect activity, e.g., a cellular signaling activity mediated by interaction of the 14815 protein with a 14815 receptor. Based on the above-described sequence structures and similarities to molecules of known function, the 14815 molecules of the present invention can have similar biological activities as kinase family members. For example, the 14815 proteins of the present invention can have one or more of the following activities: (1) the ability to bind a molecule, e.g., a nucleotide (e.g. adenosine triphosphate or guanine triphosphate); (2) the ability to bind a protein substrate, e.g. a tyrosine-containing protein or a serine or threonine-containing protein; (3) the ability to catalyze the transfer of a functional group, e.g. a phosphate, from the nucleotide to the protein, e.g. to tyrosine residue or a serine or threonine residue on the protein; (4) the ability to bind a second protein, e.g. another 14815 molecule, a different kinase, a cyclin, an ankyrin repeat-containing protein, nucleoplasmin, importin, a ras protein, or vinculin; (5) the ability to regulate transmission of signals from cellular receptors, e.g., cell growth factor receptors; (6) the ability to modulate the entry of cells, e.g., precursor cells, into the cell cycle, e.g. mitosis or meiosis; (7) the ability to modulate cellular differentiation; (8) the ability to modulate cell death, e.g. apoptosis; and (9) the ability to regulate cytoskeleton function, e.g., actin bundling.

The 14815 molecules of the invention can modulate the activities of cells in tissues where they are expressed. For example, 14815 mRNA is expressed in normal brain, normal liver, in breast tissue and primary breast tumors, but much less in metastases from the primary tumor, in resting cells, but much less in these cells stimulated with inflammatory cytokines. Accordingly, the 14815 molecules of the invention can act as therapeutic or diagnostic agents for neurological disorders, hepatic disorders, cellular proliferative and/or differentiative disorders, and inflammatory disorders.

The expression of 14815 mRNA was studied in further detail with regard to inflammation. Expression analysis of 14815 mRNA in cells of the immune system or involved in inflammatory responses showed regulation, with different amounts of 14815 expression in the resting or unstimulated cell, than the amounts in stimulated or activated cells or diseased tissue. For example, 14815 expression in resting CD8+ lymphocytes, e.g. cytotoxic T cells, is higher than in CD8+ lymphocytes, e.g. cytotoxic T cells, stimulated with anti-CD3 antibodies, so 14815 can be involved in the growth, maintenance or activity of cytotoxic T cells and play a role in allograft rejection. In another example, 14815 expression in resting normal human lung fibroblasts is higher than in normal human lung fibroblasts stimulated with transforming growth factor beta or tumor necrosis factor alpha, so 14815 can be involved in chronic conditions associated with respiratory inflammation, e.g. asthma, cystic fibrosis, chronic obstructive pulmonary disease and pulmonary fibrosis. In another example, 14815 expression in resting normal human dermal fibroblasts is higher than in normal human dermal fibroblasts stimulated with transforming growth factor beta or interleukin-1b, so 14815 can be involved in inflammatory skin conditions, such as psoriasis, allergic reactions, atopic dermatitis, and systemic sclerosis. In another example, 14815 expression in resting fibroblast-like synoviocytes is higher than in fibroblast-like synoviocytes stimulated with tumor necrosis factor alpha or interleukin-1, so 14815 can be involved in inflammatory joint conditions, such as arthritis, e.g. rheumatoid arthritis. In another example, 14815 expression in resting bronchial smooth muscle cells is higher than in bronchial smooth muscle cells stimulated with tumor necrosis factor alpha or interferon gamma, so 14815 can play a role in asthma. The expression of 14815 shows different levels in resting normal human bronchial epithelial cells compared with interleukin-4- or interleukin-13-stimulated normal human bronchial epithelial cells, so 14815 can have a role in Th2 responses, in the allergic response, in asthma, and/or in innate and adaptive immunity, e.g. in the response against nematodes or protozoa.

The 14815 molecules can be used to treat and/or diagnose neurological disorders in part because 14815 mRNA is expressed in normal brain and in part because aberrant or deficient function or expression of peroxisomal proteins can result in disorders of the nervous system. Neurological disorders include disorders of the central nervous system (CNS) and the peripheral nervous system, e.g., cognitive and neurodegenerative disorders, Examples of neurological disorders include, but are not limited to, autonomic function disorders such as hypertension and sleep disorders, and neuropsychiatric disorders, such as depression, schizophrenia, schizoaffective disorder, Korsakoff's psychosis, alcoholism, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), and bipolar affective neurological disorders, e.g., migraine and obesity. Such neurological disorders include, for example, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, *Herpes simplex* virus Type 1, *Herpes simplex* virus Type 2, Varicella-zoster virus (*Herpes zoster*), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer's disease and Pick's disease, degenerative diseases of basal ganglia and brain stem, including Parkinsonism, idiopathic Parkinson's disease (paralysis agitans) and other Lewy diffuse body diseases, progressive supranuclear palsy, corticobasal degenration, multiple system atrophy, including striatonigral degenration, Shy-Drager syndrome, and olivopontocerebellar atrophy, and Huntington's disease, senile dementia, Gilles de la Tourette's syndrome, epilepsy, and Jakob-Creutzfieldt disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, including peroxisomal disorders (e.g., Zellweger syndrome, adrenoleukodystrophy, Refsum's disease, or rhizomelic chondrodysplasia punctata), toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease. Further CNS-related disorders include, for example, those listed in the American Psychiatric Association's Diagnostic and Statistical manual of Mental Disorders (DSM), the most current version of which is incorporated herein by reference in its entirety.

The 14815 molecules can be used to treat and/or diagnose liver disorders in part because 14815 mRNA is expressed in normal liver and in part because peroxisomes are abundant in the liver. Disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e.g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome, adrenoleukodystrophy, Refsum's disease, or rhizomelic chondrodysplasia punctata). Additionally, the methods described herein can be used for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

The 14815 molecules can be used to treat and/or diagnose cellular proliferative and/or differentiative disorders in part because the 14815 mRNA is expressed in the breast tissue and primary breast tumors, but much less in metastases from the primary tumor. Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the term "cancer" (also used interchangeably with the terms, "hyperproliferative" and "neoplastic") refers to cells having the capacity for autonomous growth, i.e., an abnormal state or condition characterized by rapidly proliferating cell growth. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genitourinary tract, as well as adenocarcinomas which include malignancies such as most colon cancers, precancerous conditions and associated diseases including adenomatous polyposis of the colon and Turcot syndrome and hereditary desmoid disease, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The 14815 molecules of the invention can be used to monitor, treat and/or diagnose a variety of proliferative disorders. Such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991) Crit Rev. in Oncol./Hemotol. 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Thus, the 14815 molecules can act as novel diagnostic targets and therapeutic agents for controlling one or more cellular proliferative and/or differentiative disorders or other kinase disorders. As used herein, "kinase disorders" are diseases or disorders whose pathogenesis is caused by, is related to, or is associated with aberrant or deficient kinase protein function or expression. Examples of such disorders, e.g., kinase-associated or other 14815-associated disorders, include but are not limited to, cellular proliferative and/or differentiative disorders, as described above, as well as neurological disorders, liver disorders, apoptotic disorders, metabolic disorders and hormonal disorders.

The 14815 nucleic acid and protein of the invention can be used to treat and/or diagnose immune e.g., inflammatory (e.g. respiratory inflammatory), disorders in part because the 14815 mRNA expression is regulated by inflammatory cytokines in cells of the immune system, e.g. in CD8+ cells, and in cells which can be involved in inflammatory diseases, e.g. in lung cells (e.g. fibroblasts, bronchial epithelial cells and bronchial smooth muscle cells), in skin cells (e.g. in dermal fibroblasts), and in joint cells (e.g. in fibroblast-like synoviocytes). Examples immune and inflammatory disorders or diseases include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, inflammatory bowel disease, e.g. Crohn's disease and ulcerative colitis, aphthous ulcer, iritis, conjunctivitis, keratoconjunctivitis, asthma, allergic asthma, chronic obstructive pulmonary disease, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

The 14815 molecules can be used to treat apoptotic disorders in part because kinase family members have the ability to modulate cell death. Disorders involving aberrant or deficient apoptosis include, but are not limited to, autoimmune disorders such as systemic lupus erythematosus and immune-mediated glomerulonephritis; neoplastic disorders such as follicular lymphoma and hormone dependent tumors of the breast, prostate gland and ovary; neurodegenerative disorders, such as Alzheimer's disease, Huntington's disease, retinitis pigmentosa, amyotrophic lateral sclerosis, spinal muscular atrophy and Parkinson's disease; viral infections, such as those caused by herpesviruses, poxviruses and adenoviruses; blood disorders due to aberrant apoptotic activity in the bone marrow, such as anemia associated with chronic disease, i.e., aplastic anemia, chronic neutropenia and myelodysplasia; and tissue damage associated with myocardial infarctions and stroke.

The 14815 molecules can be used to treat metabolic disorders in part because kinase family members have the ability to regulate transmission of signals from cellular receptors. Diseases of metabolic imbalance include, but are not limited to, obesity, anorexia nervosa, cachexia, lipid disorders, and diabetes.

The 14815 molecules can be used to treat hormonal disorders in part because kinase family members have the ability to regulate transmission of signals from cellular receptors. Hormonal disorders include conditions or diseases in which the production and/or regulation of hormones in an organism is aberrant. Examples of such disorders and diseases include type I and type II diabetes mellitus, pituitary disorders (e.g., growth disorders), thyroid disorders (e.g., hypothyroidism or hyperthyroidism), and reproductive or fertility disorders (e.g., disorders which affect the organs of the reproductive system, e.g., the prostate gland, the uterus, or the vagina; disorders which involve an imbalance in the levels of a reproductive hormone in a subject; disorders affecting the ability of a subject to reproduce; and disorders affecting secondary sex characteristic development, e.g., adrenal hyperplasia).

The 14815 protein, fragments thereof, and derivatives and other variants of the sequence in SEQ ID NO:2 thereof are collectively referred to as "polypeptides or proteins of the invention" or "14815 polypeptides or proteins". Nucleic acid molecules encoding such polypeptides or proteins are collectively referred to as "nucleic acids of the invention" or "14815 nucleic acids."

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology* (1989) John Wiley & Sons, N.Y., 6.3.1–6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 14815 protein, preferably a mammalian 14815 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 14815 protein having less than about 30%, 20%, 10% and more preferably 5% (by dry weight), of non-14815 protein (also referred to herein as a "contaminating protein"), or of chemical precursors or non-14815 chemicals. When the 14815 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 14815 (e.g., the sequence of SEQ ID NO:1 or 3) without abolishing or more preferably, without substantially altering a biological activity, whereas an "essential" amino acid residue results in such a change. For example, amino acid residues that are conserved among the polypeptides of the present invention, e.g., those present in the protein kinase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 14815 protein is preferably replaced with another amino acid residue from the same side chain family. Alternatively, in another embodiment, mutations can be introduced randomly along all or part of a 14815 coding sequence, such as by saturation mutagenesis, and the resultant mutants can be screened for 14815 biological activity to identify mutants that retain activity. Following mutagenesis of SEQ ID NO:1 or SEQ ID NO:3, the encoded protein can be expressed recombinantly and the activity of the protein can be determined.

As used herein, a "biologically active portion" of a 14815 protein includes a fragment of a 14815 protein which participates in an interaction between a 14815 molecule and a non-14815 molecule. Biologically active portions of a 14815 protein include peptides comprising amino acid sequences sufficiently homologous to or derived from the amino acid sequence of the 14815 protein, e.g., the amino acid sequence shown in SEQ ID NO:2, which include fewer amino acids than the full length 14815 protein, and exhibit at least one activity of a 14815 protein. Typically, biologically active portions comprise a domain or motif with at least one activity of the 14815 protein, e.g., phosphorylation of a protein, e.g. phosphorylation of a tyrosine residue on a protein, the binding of a nucleotide, e.g. ATP, to a 14815 polypeptide, or the binding of a 14815 polypeptide to another protein, e.g. another 14815 protein, a different kinase, a cyclin, an ankyrin repeat-containing protein, nucleoplasmin, importin, a ras protein, or vinculin. A biologically active portion of a 14815 protein can be a polypeptide which is, for example, 10, 25, 50, 100, 200 or more amino acids in length. Biologically active portions of a 14815 protein can be used as targets for developing agents which modulate a 14815 mediated activity, e.g., phosphorylation of a protein, e.g. phosphorylation of a tyrosine residue on a protein, the binding of a nucleotide, e.g. ATP, to a 14815 polypeptide, or the binding of a 14815 polypeptide to another protein, e.g. another 14815 protein, a different kinase, a cyclin, an ankyrin repeat-containing protein, nucleoplasmin, importin, a ras protein, or vinculin.

Calculations of homology or sequence identity (the terms "homology" and "identity" are used interchangeably herein) between sequences are performed as follows:

To determine the percent identity of two amino acid sequences, or of two nucleic acid sequences, the sequences are aligned for optimal comparison purposes (e.g., the relative positions of the aligned sequences is set so areas of highest identity coincide, i.e. N-termini of the sequences do not necessarily coincide). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 14815 amino acid sequence of SEQ ID NO:2 having 1115 amino acid residues, at least 334, preferably at least 446, more preferably at least 557, even more preferably at least 669, and even more preferably at least 780, 892, or 1003 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

In one embodiment, e.g. in a global alignment, the calculation of percent identity accounts for the full length of the sequence of the invention, e.g. the full length 14815 polypeptide of SEQ ID NO:2 (e.g. 1115 amino acids in length). In another embodiment, e.g. in a gapped alignment, the calculation of percent identity accounts only for the portions of high identity contained by both sequences, with gaps introduced in one or both sequences to ignore regions of low identity or missing sequences. The percent identity between the two sequences in a gapped alignment thus is a function of the number of identical positions shared by the sequences, taking into account the number of gaps, and the length of each gap, which need to be introduced for optimal alignment of the two sequences. For example, two sequences have 10 contiguous identical amino acids, but one sequence additionally has 10 contiguous amino acids at its N-terminus. A global alignment of the 10 amino acid sequence with the 20 amino acid sequence, accounting for the 10 additional amino acids, can give a result of 55% identity, but a gapped alignment of these sequences, discounting for the 10 additional amino acids, can give a result of 100% identity.

The comparison of sequences and determination of percent identity between two sequences can be accomplished using a mathematical algorithm. In a preferred embodiment, e.g. for a global alignment, the percent identity between two amino acid or nucleotide sequences can be determined using the algorithm of Meyers and Miller ((1989) CABIOS, 4:11–17) which has been incorporated into the ALIGN program (version 2.0), using a PAM120 weight residue table, Blosum 50 matrix, a gap length penalty of 12 and a gap penalty of 4. By the global alignment calculation, 14815 polypeptides can have at least 60%, 65%, 75%, 85%, 90%, 91%, 92%, 93%, 94%, 95%, 96%, 97%, 98% or 99% identity to the amino acid sequence of SEQ ID NO:2.

In another embodiment, e.g. for a gapped alignment, the percent identity between two amino acid sequences is determined using the Needleman and Wunsch (1970) *J. Mol.*

*Biol.* 48:444–453 algorithm which has been incorporated into the GAP program in the GCG software package (available at the bioinformatics page of the website maintained by Accelrys, Inc., San Diego, Calif., USA), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the bioinformatics page of the website maintained by Accelrys, Inc., San Diego, Calif., USA) using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (1990) *J. Mol. Biol.* 215:403–10. BLAST nucleotide searches can be performed with the NBLAST program, score=100, wordlength=12 to obtain nucleotide sequences homologous to 14815 nucleic acid molecules of the invention. BLAST protein searches can be performed with the XBLAST program, score=50, wordlength=3 to obtain amino acid sequences homologous to 14815 protein molecules of the invention. To obtain gapped alignments for comparison purposes, Gapped BLAST can be utilized as described in Altschul et al., (1997) *Nucleic Acids Res.* 25:3389–3402. When utilizing BLAST and Gapped BLAST programs, the default parameters of the respective programs (e.g., XBLAST and NBLAST) can be used (accessible at the website maintained by National Center for Biotechnology Information, Bethesda, Md., USA (ncbi.nlm.nih.gov)).

Particular 14815 polypeptides of the present invention have an amino acid sequence substantially identical to the amino acid sequence of SEQ ID NO:2. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 60%, or 65% identity, likely 75% identity, more likely 85%, 90%, 91%, 92%, 93%, 94%, 95%, 96%, 97%, 98% or 99% identity, as calculated by a global alignment, to SEQ ID NO:2 are termed substantially identical.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 60%, or 65% identity, likely 75% identity, more likely 85%, 90%. 91%, 92%, 93%, 94%, 95%, 96%, 97%, 98% or 99% identity, as calculated by a global alignment, to SEQ ID NO:1 or 3 are termed substantially identical.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 14815 polypeptide described herein, e.g., a full length 14815 protein or a fragment thereof, e.g., a biologically active portion of 14815 protein. Also included is a nucleic acid fragment suitable for use as a hybridization probe, which can be used, e.g., to identify a nucleic acid molecule encoding a polypeptide of the invention, 14815 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of any of this nucleotide sequence. In one embodiment, the nucleic acid molecule includes sequences encoding the human 14815 protein (i.e., "the coding region" of SEQ ID NO:1, as shown in SEQ ID NO:3), as well as 5' untranslated sequences (nucleotides 1 to 182 of SEQ ID NO:1) and 3' untranslated sequences (nucleotides 3531 to 3919 of SEQ ID NO:1). Alternatively, the nucleic acid molecule can include only the coding region of SEQ ID NO:1 (e.g., SEQ ID NO:3) and, e.g., no flanking sequences which normally accompany the subject sequence. In another embodiment, the nucleic acid molecule encodes a sequence corresponding to a fragment of the protein from about amino acid 519 to 779 of SEQ ID NO:2, or a fragment thereof, e.g. about amino acid residues 519 to 600, 601 to 700, or 701 to 779 of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3 such that it can hybridize to the nucleotide sequence shown in SEQ ID NO:1 or 3, thereby forming a stable duplex.

In one embodiment, an isolated nucleic acid molecule of the present invention includes a nucleotide sequence which is at least about: 60%, 65%, 70%, 75%, 80%, 85%, 90%, 91%, 92%, 93%, 94%, 95%, 96%, 97%, 98%, 99%, or more homologous to the entire length of the nucleotide sequence shown in SEQ ID NO: I or SEQ ID NO:3, or a portion, preferably of the same length, of any of these nucleotide sequences.

14815 Nucleic Acid Fragments

A nucleic acid molecule of the invention can include only a portion of the nucleic acid sequence of SEQ ID NO:1 or 3. For example, such a nucleic acid molecule can include a fragment which can be used as a probe or primer or a fragment encoding a portion of a 14815 protein, e.g., an immunogenic or biologically active portion of a 14815 protein. A fragment can comprise those nucleotides of SEQ ID NO:1, which encode a protein kinase domain of human 14815. The nucleotide sequence determined from the cloning of the 14815 gene allows for the generation of probes and primers designed for use in identifying and/or cloning other 14815 family members, or fragments thereof, as well as 14815 homologs, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 260 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, a 14815 nucleic acid fragment can include a sequence corresponding to a protein kinase domain, as described herein.

14815 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes: a protein kinase domain at about amino acid residues 519 to 779 of SEQ ID NO:2, or an armadillo/beta-catenin-like repeat domain at about amino acid residues 198 to 238, 239 to 279, 280 to 320, and 401 to 448 of SEQ ID NO:2. For example, a 14815 probe or primer can comprise SEQ ID NO:10, SEQ ID NO:11 or SEQ ID NO:12.

In another embodiment a set of primers is provided, e.g., primers suitable for use in a PCR, which can be used to amplify a selected region of a 14815 sequence, e.g., a domain, region, site or other sequence described herein. The primers should be at least 5, 10, or 50 base pairs in length and less than 100, or less than 200, base pairs in length. The primers should be identical, or differ by one base from a sequence disclosed herein or from a naturally occurring variant. For example, primers suitable for amplifying all or a portion of any of the following regions are provided: a protein kinase domain from about amino acid 519 to 779 of SEQ ID NO:2, or an armadillo/beta-catenin-like repeat domain at about amino acid residues 198 to 238, 239 to 279, 280 to 320, and 401 to 448 of SEQ ID NO:2.

A nucleic acid fragment can encode an epitope bearing region of a polypeptide described herein. Such a fragment, e.g. an antigenic fragment, can comprise a biologically active portion of an 14815 polypeptide, as described below, or a subportion thereof, e.g. at least 8, 9, 10, 11, 12, 13, 15, 20, 30 or more amino acid residues of SEQ ID NO:2. Thus, the fragment can comprise at least 24, 27, 30, 33, 36, 39, 45, 60, 90, or more bases. Such fragments are described in more detail in the "Anti-14815 Antibodies" section below.

A nucleic acid fragment encoding a "biologically active portion of a 14815 polypeptide" can be prepared by isolating a portion of the nucleotide sequence of SEQ ID NO:1 or 3, which encodes a polypeptide having a 14815 biological activity (e.g., the biological activities of the 14815 proteins are described herein), expressing the encoded portion of the 14815 protein (e.g., by recombinant expression in vitro) and assessing the activity of the encoded portion of the 14815 protein. For example, a nucleic acid fragment encoding a biologically active portion of 14815 includes a protein kinase domain, e.g., amino acid residues about 519 to 779 of SEQ ID NO:2, a coiled coil structure, e.g., amino acid residues about 472 to 500 of SEQ ID NO:2, or an armadillo/beta-catenin-like repeat domain at about amino acid residues 198 to 238, 239 to 279, 280 to 320, and 401 to 448 of SEQ ID NO:2. A nucleic acid fragment encoding a biologically active portion of a 14815 polypeptide, can comprise a nucleotide sequence which is greater than 69, 72, 84, 87, 120, 123, 780 or more nucleotides in length. Such a fragment can encode a polypeptide which at least can bind a nucleotide, e.g. ATP or GTP, or another protein, e.g. another 14815 molecule, a different kinase, a cyclin, an ankyrin repeat-containing protein, nucleoplasmin, importin, a ras protein, or vinculin, or a protein or polypeptide with a tyrosine residue.

In preferred embodiments, a nucleic acid includes a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900 or more nucleotides in length and hybridizes under stringent hybridization conditions to a nucleic acid molecule of SEQ ID NO:1 or SEQ ID NO:3.

14815 Nucleic Acid Variants

The invention further encompasses nucleic acid molecules that differ from the nucleotide sequence shown in SEQ ID NO:1 or SEQ ID NO:3. Such differences can be due to degeneracy of the genetic code (and result in a nucleic acid which encodes the same 14815 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the inventor can be chosen for having codons, which are preferred, or non-preferred, for a particular expression system. E.g., the nucleic acid can be one in which at least one codon, at preferably at least 10%, or 20% of the codons has been altered such that the sequence is optimized for expression in *E. coli*, yeast, human, insect, or CHO cells.

Nucleic acid variants can be naturally occurring, such as allelic variants (same locus), homologs (different locus), and orthologs (different organism) or can be non naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or 3, e.g., as follows: by at least one but less than 10, 20, 30, or 40 nucleotides; at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the nucleotide sequence shown in SEQ ID NO:2 or a fragment of this sequence. Such nucleic acid molecules can readily be identified as being able to hybridize under stringent conditions, to the nucleotide sequence shown in SEQ ID NO 2 or a fragment of the sequence. Nucleic acid molecules corresponding to orthologs, homologs, and allelic variants of the 14815 cDNAs of the invention can further be isolated by mapping to the same chromosome or locus as the 14815 gene. For example, the 14815 gene can be found on human chromosome 14.

Preferred variants include those that are correlated with phosphorylation of a protein, e.g. phosphorylation of a tyrosine residue on a protein, the binding of a nucleotide, e.g. ATP or GTP, or the binding of another protein, e.g. another 14815 molecule, a different kinase, a cyclin, an ankyrin repeat-containing protein, nucleoplasmin, importin, a ras protein, or vinculin, or a protein or polypeptide with a tyrosine residue.

Allelic variants of 14815, e.g., human 14815, include both functional and non-functional proteins. Functional allelic variants are naturally occurring amino acid sequence variants of the 14815 protein within a population that maintain the ability to bind a molecule, e.g., a nucleotide (e.g. adenosine triphosphate or guanine triphosphate) and catalyze the transfer of a functional group, e.g. a phosphate, from the nucleotide to a protein, e.g. to a tyrosine, serine or threonine residue on the protein; the ability to modulate the cell cycle or cell death. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 14815, e.g., human 14815, protein within a population that do not have the ability to bind a molecule, e.g., a nucleotide (e.g. adenosine triphosphate or guanine triphosphate) and catalyze the transfer of a functional group, e.g. a phosphate, from the nucleotide to a protein, e.g. to a tyrosine, serine or threonine residue on the protein; the ability to modulate the cell cycle or cell death. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein. For example, changes can be made in the protein kinase domain, in one, two, three, or four armadillo/beta-catenin-like repeat domains of 14815 protein kinase. As an example of a change in the protein kinase domain, nucleotides in the codon encoding K-548 of SEQ ID NO:2 can be changed, e.g. changes in nucleotides 1824 and 1825 of SEQ ID NO:1 or nucleotides 1642 or 1643 of SEQ ID NO:3 can inhibit a biological activity, e.g. protein phosphorylation activity, e.g. nucleotide (e.g. ATP or GTP) binding activity, of a 14815 polypeptide. As another example, nucleotides in the codon encoding D-655 of SEQ ID NO:2 can be changed, e.g. changes in nucleotides 2146 and 2147 of SEQ ID NO:1 or nucleotides 1963 and 1964 of SEQ ID NO:3 can inhibit a biological activity, e.g. protein phosphorylation activity, of a 14815 polypeptide. In another example, nucleotides in regions of SEQ ID NO:1 or SEQ ID NO:3 encoding the coiled coil structure, e.g. nucleotides encoding amino acid residues in regions amino acids residues 472 to 500 of SEQ ID NO:2 can be changed to alter oligomerization or protein binding of a 14815 protein. In further examples, nucleotides in regions of SEQ ID NO:1 or SEQ ID NO:3 encoding one or more of the armadillo/beta-catenin-like repeat domains, e.g. nucleotides encoding amino acid residues in regions of amino acids 198 to 238, 239 to 279, 280 to 320, and 401 to 448 of SEQ ID NO:2 can be changed to alter protein binding, e.g. binding to another protein, e.g. another 14815 molecule, a different kinase, a cyclin, an ankyrin repeat-containing protein, nucleoplasmin, importin, a ras protein, or vinculin, or a protein or polypeptide with a tyrosine residue of a 14815 polypeptide. Following mutagenesis, the encoded protein can be expressed recombinantly, and the activity of the protein can be determined using standard assay techniques.

Moreover, nucleic acid molecules encoding other 14815 family members and, thus, which have a nucleotide sequence which differs from the 14815 sequences of SEQ ID NO:1 or SEQ ID NO:3 are intended to be within the scope of the invention.

Antisense Nucleic Acid Molecules, Ribozymes and Modified 14815 Nucleic Acid Molecules In another aspect, the invention features, an isolated nucleic acid molecule which is antisense to 14815. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 14815 coding strand, or to only a portion thereof (e.g., the coding region of human 14815 corresponding to SEQ ID NO:3). In another embodiment, the antisense nucleic acid molecule is antisense to a "noncoding region" of the coding strand of a nucleotide sequence encoding 14815 (e.g., the 5' and 3' untranslated regions).

An antisense nucleic acid can be designed such that it is complementary to the entire coding region of 14815 mRNA, but more preferably is an oligonucleotide which is antisense to only a portion of the coding or noncoding region of 14815 mRNA. For example, the antisense oligonucleotide can be complementary to the region surrounding the translation start site of 14815 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 14815 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically or selectively bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. A ribozyme having specificity for a 14815-encoding nucleic acid can include one or more sequences complementary to the nucleotide sequence of a 14815 cDNA disclosed herein (i.e., SEQ ID NO:1 or SEQ ID NO:3), and a sequence having known catalytic sequence responsible for mRNA cleavage (see U.S. Pat. No. 5,093, 246 or Haselhoff and Gerlach (1988) *Nature* 334:585–591). For example, a derivative of a *Tetrahymena* L-19 IVS RNA can be constructed in which the nucleotide sequence of the active site is complementary to the nucleotide sequence to be cleaved in a 14815-encoding mRNA. See, e.g., Cech et al. U.S. Pat. No. 4,987,071; and Cech et al. U.S. Pat. No. 5,116,742. Alternatively, 14815 mRNA can be used to select a catalytic RNA having a specific ribonuclease activity from a pool of RNA molecules. See, e.g., Bartel and Szostak (1993) *Science* 261:1411–1418.

14815 gene expression can be inhibited by targeting nucleotide sequences complementary to the regulatory region of the 14815 (e.g., the 14815 promoter and/or enhancers) to form triple helical structures that prevent transcription of the 14815 gene in target cells. See generally, Helene (1991) *Anticancer Drug Des.* 6:569–84; Helene (1992) *Ann. N.Y. Acad. Sci.* 660:27–36; and Maher (1992) *Bioassays* 14:807–15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 14815 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. (1996) *Proc. Natl. Acad. Sci.* 93: 14670–675.

PNAs of 14815 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 14815 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup et al. (1996) supra)); or as probes or primers for DNA sequencing or hybridization (Hyrup et al. (1996) supra; Perry-O'Keefe supra).

In other embodiments, the oligonucleotide can include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (see, e.g., Krol et al. (1988) *Bio-Techniques* 6:958–976) or intercalating agents. (see, e.g., Zon (1988) *Pharm. Res.* 5:539–549). To this end, the oligonucleotide can be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 14815 nucleic acid of the invention, two complementary regions one having a fluorophore and one a quencher such that the molecular beacon is useful for quantitating the presence of the 14815 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 14815 Polypeptides

In another aspect, the invention features, an isolated 14815 protein, or fragment, e.g., a biologically active portion, for use, e.g., in screening assays, as therapeutic or diagnostic targets, or as immunogens or antigens to raise or test (or more generally to bind) anti-14815 antibodies. 14815 protein can be isolated from cells or tissue sources using standard protein purification techniques. 14815 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and post-translational events. The polypeptide can be expressed in systems, e.g., cultured cells, which result in substantially the same post-translational modifications present when the polypeptide is expressed in a native cell, or in systems which result in the alteration or omission of post-translational modifications, e.g., glycosylation or cleavage, present in a native cell.

In a preferred embodiment, a 14815 polypeptide has one or more of the following characteristics:

it has the ability to bind a molecule, e.g., a nucleotide (e.g. adenosine triphosphate or guanine triphosphate);

the ability to bind a protein substrate, e.g. a tyrosine, serine or threonine-containing protein;

the ability to catalyze the transfer of a functional group, e.g. a phosphate, from the nucleotide to the protein, e.g. to a tyrosine, serine or threonine residue on the protein;

the ability to bind a second protein, e.g. another 14815 molecule, a different kinase, a cyclin, an ankyrin repeat-containing protein, nucleoplasmin, importin, a ras protein, or vinculin;

the ability to regulate transmission of signals from cellular receptors, e.g., cell growth factor receptors;

the ability to modulate the entry of cells, e.g., precursor cells, into the cell cycle, e.g. mitosis or meiosis;

the ability to modulate cell death, e.g. apoptosis;

it has a molecular weight, e.g., a deduced molecular weight, preferably ignoring any contribution of post translational modifications, amino acid composition or other physical characteristic of a 14815 polypeptide, e.g., a polypeptide of SEQ ID NO:2;

it has an overall sequence identity of at least 60%, preferably at least 70%, more preferably at least 80, 90, or 95%, as calculated by a global alignment, with a polypeptide of SEQ ID NO:2;

it can be found in breast tissue and primary breast tumors, but much less in metastases from the primary tumor;

it has a protein kinase domain which is preferably about 70%, 80%, 90% or 95% identical to amino acid residues about 519 to 779 of SEQ ID NO:2;

it has at least one, two, three, preferably four armadillo/beta-catenin-like repeat domains which are preferably about 70%, 80%, 90% or 95% identical to amino acid residues about 198 to 238, 239 to 279, 280 to 320, and 401 to 448 of SEQ ID NO:2;

In a preferred embodiment, the 14815 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment, the differences are not in the protein kinase domain at about residues 519 to 779 of SEQ ID NO:2 or in one of the armadillo/beta-catenin-like repeat domains at about residues 198 to 238, 239 to 279, 280 to 320, and 401 to 448 of SEQ ID NO:2. In another embodiment one or more differences are in the protein kinase domain at about residues 519 to 779 of SEQ ID NO:2 or in one of the armadillo/beta-catenin-like repeat domains at about residues 198 to 238, 239 to 279, 280 to 320, and 401 to 448 of SEQ ID NO:2.

Other embodiments include a protein that contains one or more changes in amino acid sequence, e.g., a change in an amino acid residue which is not essential for activity. Such 14815 proteins differ in amino acid sequence from SEQ ID NO:2, yet retain biological activity.

In one embodiment, the protein includes an amino acid sequence at least about 60%, 65%, 70%, 75%, 80%, 85%, 90%, 95%, 98% or more homologous to SEQ ID NO:2 as calculated by a global alignment. In another embodiment, the protein includes fragments or regions homologous to fragments, at least about 70%, 80%, 90%, 95%, 96%, 97%, 98%, 99% or more homologous to a fragment of SEQ ID NO:2, as calculated by a gapped alignment. A fragment of a 14815 protein can be a domain, e.g. a protein kinase domain at about residues 519 to 779 of SEQ ID NO:2 or a fragment thereof, e.g. about amino acid residues 519 to 600, 601 to 700, or 701 to 779 of SEQ ID NO:2, a coiled coil structure, e.g. about amino acid residues 472 to 500 of SEQ ID NO:2, or an armadillo/beta-catenin-like repeat domain, e.g. at about residues 198 to 238, 239 to 279, 280 to 320, and 401 to 448 of SEQ ID NO:2.

A 14815 protein or fragment is provided which varies from the sequence of SEQ ID NO:2 in regions defined by amino acids about 1 to 519 or 780 to 1115 by at least one but by less than 15, 10 or 5 amino acid residues in the protein or fragment but which does not differ from SEQ ID NO:2 in regions defined by amino acids about 519 to 779. (If this comparison requires alignment the sequences should be aligned for maximum homology. "Looped" out sequences from deletions or insertions, or mismatches, are considered differences.) In some embodiments the difference is at a non-essential residue or is a conservative substitution, while in others the difference is at an essential residue or is a non-conservative substitution.

In one embodiment, a biologically active portion of a 14815 protein includes a protein kinase domain. In other embodiments, biologically active portions of a 14815 protein include at least one armadillo/beta-catenin-like repeat domain or a coiled coil structure. Moreover, other biologically active portions, in which other regions of the protein are deleted, can be prepared by recombinant techniques and evaluated for one or more of the functional activities of a native 14815 protein.

In a preferred embodiment, the 14815 protein has an amino acid sequence shown in SEQ ID NO:2. In other embodiments, the 14815 protein is sufficiently or substantially identical to SEQ ID NO:2. In yet another embodiment, the 14815 protein is sufficiently or substantially identical to SEQ ID NO:2 and retains the functional activity of the protein of SEQ ID NO:2, as described in detail in the subsections above.

14815 Chimeric or Fusion Proteins

In another aspect, the invention provides 14815 chimeric or fusion proteins. As used herein, a 14815 "chimeric protein" or "fusion protein" includes a 14815 polypeptide linked to a non-14815 polypeptide. A "non-14815 polypeptide" refers to a polypeptide having an amino acid sequence corresponding to a protein which is not substantially homologous to the 14815 protein, e.g., a protein which is different from the 14815 protein and which is derived from the same or a different organism. The 14815 polypeptide of the fusion protein can correspond to all or a portion e.g., a fragment described herein of a 14815 amino acid sequence, e.g. a domain, e.g. a protein kinase domain or a fragment thereof, e.g. about amino acid residues 519 to 779, 519 to 600, 601 to 700, or 701 to 779 of SEQ ID NO:2, a coiled coil structure, e.g. about amino acid residues 472 to 500 of SEQ ID NO:2, or an armadillo/beta-catenin-like repeat domain, e.g. at about residues 198 to 238, 239 to 279, 280 to 320, and 401 to 448 of SEQ ID NO:2. In a preferred embodiment, a 14815 fusion protein includes at least one (or two) biologically active portion of a 14815 protein. The non-14815 polypeptide can be fused to the N-terminus or C-terminus of the 14815 polypeptide.

The fusion protein can include a moiety which has a high affinity for a ligand. For example, the fusion protein can be a GST-14815 fusion protein in which the 14815 sequences are fused to the C-terminus of the GST sequences. Such fusion proteins can facilitate the purification of recombinant 14815. Alternatively, the fusion protein can be a 14815 protein containing a heterologous signal sequence at its N-terminus. In certain host cells (e.g., mammalian host cells), expression and/or secretion of 14815 can be increased through use of a heterologous signal sequence.

Fusion proteins can include all or a part of a serum protein, e.g., a portion of an immunoglobulin (e.g., IgG, IgA, or IgE), e.g., an Fe region and/or the hinge C1 and C2 sequences of an immunoglobulin or human serum albumin.

The 14815 fusion proteins of the invention can be incorporated into pharmaceutical compositions and administered to a subject in vivo. The 14815 fusion proteins can be used to affect the bioavailability of a 14815 substrate. 14815 fusion proteins can be useful therapeutically for the treatment of disorders caused by, for example, (i) aberrant modification or mutation of a gene encoding a 14815 protein; (ii) mis-regulation of the 14815 gene; and (iii) aberrant post-translational modification of a 14815 protein.

Moreover, the 14815-fusion proteins of the invention can be used as immunogens to produce anti-14815 antibodies in a subject, to purify 14815 ligands and in screening assays to identify molecules which inhibit the interaction of 14815 with a 14815 substrate.

Expression vectors are commercially available that already encode a fusion moiety (e.g., a GST polypeptide). A 14815-encoding nucleic acid can be cloned into such an expression vector such that the fusion moiety is linked in-frame to the 14815 protein.

Variants of 14815 Proteins

In another aspect, the invention also features a variant of a 14815 polypeptide, e.g., which functions as an agonist (mimetics) or as an antagonist. Variants of the 14815 proteins can be generated by mutagenesis, e.g., discrete point mutation, the insertion or deletion of sequences or the truncation of a 14815 protein. An agonist of the 14815 proteins can retain substantially the same, or a subset, of the biological activities of the naturally occurring form of a 14815 protein. An antagonist of a 14815 protein can inhibit one or more of the activities of the naturally occurring form of the 14815 protein by, for example, competitively modulating a 14815-mediated activity of a 14815 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 14815 protein.

Variants of a 14815 protein can be identified by screening combinatorial libraries of mutants, e.g., truncation mutants, of a 14815 protein for agonist or antagonist activity.

Libraries of fragments e.g., N terminal, C terminal, or internal fragments, of a 14815 protein coding sequence can be used to generate a variegated population of fragments for screening and subsequent selection of variants of a 14815 protein.

Variants in which a cysteine residues is added or deleted or in which a residue which is glycosylated is added or deleted are particularly preferred.

Other variants can alter, eliminate or inhibit the biological activity (e.g. the protein kinase activity) of the 14815 polypeptide set forth in SEQ ID NO:2. For example, a variant of a 14815 polypeptide can have an amino acid other than K at position 548 or a variant can have an amino acid other than D at position 655 of SEQ ID NO:2 such that the resulting polypeptide does not have protein kinase activity.

Methods for screening gene products of combinatorial libraries made by point mutations or truncation, and for screening cDNA libraries for gene products having a selected property are known in the art. Recursive ensemble mutagenesis (REM), a new technique which enhances the frequency of functional mutants in the libraries, can be used in combination with the screening assays to identify 14815 variants (Arkin and Yourvan (1992) *Proc. Natl. Acad. Sci. USA* 89:7811–7815; Delgrave et al. (1993) *Protein Engineering* 6:327–331).

Cell based assays can be exploited to analyze a variegated 14815 library. For example, a library of expression vectors can be transfected into a cell line, e.g., a cell line, which ordinarily responds to 14815 in a substrate-dependent manner. The transfected cells are then contacted with 14815 and the effect of the expression of the mutant on signaling by the 14815 substrate can be detected, e.g., by measuring phosphorylation of a protein, e.g. phosphorylation of a tyrosine residue on a protein, the binding of a nucleotide, e.g. ATP or GTP, to a 14815 polypeptide, or the binding of a 14815 polypeptide to another protein, e.g. another 14815 protein, a different kinase, a cyclin, an ankyrin repeat-containing protein, nucleoplasmin, importin, a ras protein, or vinculin. Plasmid DNA can then be recovered from the cells which score for inhibition, or alternatively, potentiation of signaling by the 14815 substrate, and the individual clones further characterized.

In another aspect, the invention features a method of making a 14815 polypeptide, e.g., a peptide having a non-wild type activity, e.g., an antagonist, agonist, or super agonist of a naturally occurring 14815 polypeptide, e.g., a naturally occurring 14815 polypeptide. The method includes altering the sequence of a 14815 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 14815 polypeptide a biological activity of a naturally occurring 14815 polypeptide. The method includes altering the sequence, e.g., by substitution or deletion of one or more residues, of a 14815 polypeptide, e.g., altering the sequence of a non-conserved region, or a domain or residue described herein, and testing the altered polypeptide for the desired activity.

Anti-14815 Antibodies

In another aspect, the invention provides an anti-14815 antibody. The term "antibody" as used herein refers to an immunoglobulin molecule or immunologically active portion thereof, i.e., an antigen-binding portion. Examples of immunologically active portions of immunoglobulin molecules include scFV and dcFV fragments, Fab and F(ab')$_2$ fragments which can be generated by treating the antibody with an enzyme such as papain or pepsin, respectively.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 14815 protein or, antigenic peptide fragment of 14815 can be used as an immunogen or can be used to identify anti-14815 antibodies made with other immunogens, e.g., cells, membrane preparations, and the like. The antigenic peptide of 14815 should include at least 8 amino acid residues of the amino acid sequence shown in SEQ ID NO:2 and encompasses an epitope of 14815. Preferably, the antigenic peptide includes at least 10 amino acid residues, more preferably at least 15 amino acid residues, even more preferably at least 20 amino acid residues, and most preferably at least 30 amino acid residues.

Fragments of 14815 which include residues about 51 to 61, from about 90 to 104, and from about 802 to 815 of SEQ ID NO:2 can be used to make, e.g., used as immunogens or used to characterize the specificity of an antibody, antibodies against hydrophilic regions of the 14815 protein (see FIG. 1). Similarly, fragments of 14815 which include residues about 135 to 143, from about 225 to 237, and from about 634 to 642 of SEQ ID NO:2 can be used to make an antibody against a hydrophobic region of the 14815 protein; fragments of 14815 which include residues about 1 to 50, about 105 to 197, about 321 to 400, about 450 to 515, about 780 to 900, about 901 to 1000 or about 1001 to 1115 of SEQ ID NO:2 can be used to make an antibody against an intracellular region of the 14815 protein; a fragment of 14815 which includes residues about 519 to 600, about 601 to 700, or about 701 to 779 of SEQ ID NO:2 can be used to make an antibody against the protein kinase region of the 14815 protein; a fragment of 14815 which includes about residues 198 to 238, about 239 to 279, about 280 to 320, and about 401 to 448 of SEQ ID NO:2 can be used to make an antibody against an armadillo/beta-catenin-like repeat domain of the 14815 protein.

Antibodies reactive with, or specific or selective for, any of these regions, or other regions or domains described herein are provided.

Preferred epitopes encompassed by the antigenic peptide are regions of 14815 located on the surface of the protein, e.g., hydrophilic regions, as well as regions with high antigenicity. For example, an Emini surface probability analysis of the human 14815 protein sequence can be used to indicate the regions that have a particularly high probability of being localized to the surface of the 14815 protein and are thus likely to constitute surface residues useful for targeting antibody production.

In a preferred embodiment the antibody binds an epitope on any domain or region on 14815 proteins described herein.

Additionally, chimeric, humanized, and completely human antibodies are also within the scope of the invention. Chimeric, humanized, but most preferably, completely human antibodies are desirable for applications which include repeated administration, e.g., therapeutic treatment of human patients, and some diagnostic applications.

Chimeric and humanized monoclonal antibodies, comprising both human and non-human portions, can be made using standard recombinant DNA techniques. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041–1043; Liu et al. (1987) Proc. Natl. Acad. Sci. USA 84:3439–3443; Liu et al. (1987) J. Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559).

A humanized or complementarity determining region (CDR)-grafted antibody will have at least one or two, but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody to a 14815 or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, (1987) From Genes to Clones (Verlagsgesellschaft, Weinheim, Germany). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison (1985) *Science* 229:1202–1207, by Oi et al. (1986) *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a 14815 polypeptide or fragment thereof. The recombinant DNA encoding the humanized antibody, or fragment thereof, can then be cloned into an appropriate expression vector.

Humanized or CDR-grafted antibodies can be produced by CDR-grafting or CDR substitution, wherein one, two, or all CDR's of an immunoglobulin chain can be replaced. See e.g., U.S. Pat. No. 5,225,539; Jones et al. (1986) *Nature* 321:552–525; Verhoeyan et al. (1988) *Science* 239:1534; Beidler et al. (1988) *J. Immunol.* 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12–16 of U.S. Pat. No. 5,585,089, the e.g., columns 12–16 of U.S. Pat. No. 5,585, 089, the contents of which are hereby incorporated by reference. Other techniques for humanizing antibodies are described in Padlan et al. EP 519596 A1, published on Dec. 23, 1992.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol.* 13:65–93); and U.S. Pat. Nos. 5,625,126; 5,633,425; 5,569,825; 5,661,016; and 5,545,806. In addition, companies such as Abgenix, Inc. (Fremont, Calif.) and Medarex, Inc. (Princeton, N.J.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

The anti-14815 antibody can be a single chain antibody. A single-chain antibody (scFV) can be engineered as described in, for example, Colcher et al. (1999) *Ann. N Y Acad. Sci.* 880:263–80; and Reiter (1996) *Clin. Cancer Res.* 2:245–52. The single chain antibody can be dimerized or multimerized to generate multivalent antibodies having specificities for different epitopes of the same target 14815 protein.

In a preferred embodiment, the antibody has reduced or no ability to bind an Fc receptor. For example, it is an isotype or subtype, fragment or other mutant, which does not support binding to an Fc receptor, e.g., it has a mutagenized or deleted Fc receptor binding region.

An antibody (or fragment thereof) may be conjugated to a therapeutic moiety such as a cytotoxin, a therapeutic agent or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208, 020), CC-1065 (see U.S. Pat. Nos. 5,475,092, 5,585,499, 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioactive ions include, but are not limited to iodine, yttrium and praseodymium.

The conjugates of the invention can be used for modifying a given biological response, the therapeutic moiety is not to be construed as limited to classical chemical therapeutic agents. For example, the therapeutic moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

An anti-14815 antibody (e.g., monoclonal antibody) can be used to isolate 14815 by standard techniques, such as affinity chromatography or immunoprecipitation. Moreover, an anti-14815 antibody can be used to detect 14815 protein (e.g., in a cellular lysate or cell supernatant) in order to evaluate the abundance and pattern of expression of the protein. Anti-14815 antibodies can be used diagnostically to monitor protein levels in tissue as part of a clinical testing procedure, e.g., to determine the efficacy of a given treatment regimen. Detection can be facilitated by coupling (i.e., physically linking) the antibody to a detectable substance (i.e., antibody labelling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In preferred embodiments, an antibody can be made by immunizing with a purified 14815 antigen, or a fragment thereof, e.g., a fragment described herein, a membrane associated antigen, tissues, e.g., crude tissue preparations, whole cells, preferably living cells, lysed cells, or cell fractions, e.g., cytosolic supernatants, membrane fractions or peroxisomal fractions.

Antibodies which bind only a native 14815 protein, only denatured or otherwise non-native 14815 protein, or which bind both, are within the invention. Antibodies with linear or conformational epitopes are within the invention. Conformational epitopes sometimes can be identified by identifying antibodies which bind to native but not denatured 14815 protein.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 14815 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 14815 proteins, mutant forms of 14815 proteins, fusion proteins, and the like).

The recombinant expression vectors of the invention can be designed for expression of 14815 proteins in prokaryotic or eukaryotic cells. For example, polypeptides of the invention can be expressed in E. coli, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 14815 activity assays, (e.g., direct assays or competitive assays described in detail below), or to generate antibodies specific or selective for 14815 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in E. coli is to express the protein in a host bacteria with an impaired capacity to proteolytically cleave the recombinant protein (Gottesman (1990) *Gene Expression Technology: Methods in Enzymology* 185, Academic Press, San Diego, Calif. 119–128). Another strategy is to alter the nucleic acid sequence of the nucleic acid to be inserted into an expression vector so that the individual codons for each amino acid are those preferentially utilized in E. coli (Wada et al., (1992) *Nucleic Acids Res.* 20:2111–2118). Such alteration of nucleic acid sequences of the invention can be carried out by standard DNA synthesis techniques.

The 14815 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988)

Adv. Immunol. 43:235–275), in particular promoters of T cell receptors (Winoto and Baltimore (1989) EMBO J. 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) Proc. Natl. Acad. Sci. USA 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) Science 249:374–379) and the α-fetoprotein promoter (Campes and Tilghman (1989) Genes Dev. 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al., (1986) Reviews—Trends in Genetics 1:1.

Another aspect the invention provides a host cell which includes a nucleic acid molecule described herein, e.g., a 14815 nucleic acid molecule within a recombinant expression vector or a 14815 nucleic acid molecule containing sequences which allow it to homologously recombine into a specific site of the host cell's genome. The terms "host cell" and "recombinant host cell" are used interchangeably herein. Such terms refer not only to the particular subject cell but also to the progeny or potential progeny of such a cell. Because certain modifications can occur in succeeding generations due to either mutation or environmental influences, such progeny may not, in fact, be identical to the parent cell, but are still included within the scope of the term as used herein.

A host cell can be any prokaryotic or eukaryotic cell. For example, a 14815 protein can be expressed in bacterial cells such as E. coli, insect cells, yeast or mammalian cells (such as Chinese hamster ovary (CHO) cells or CV-1 origin, SV-40 (COS) cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 14815 protein. Accordingly, the invention further provides methods for producing a 14815 protein using the host cells of the invention. In one embodiment, the method includes culturing the host cell of the invention (into which a recombinant expression vector encoding a 14815 protein has been introduced) in a suitable medium such that a 14815 protein is produced. In another embodiment, the method further includes isolating a 14815 protein from the medium or the host cell.

In another aspect, the invention features, a cell or purified preparation of cells which include a 14815 transgene, or which otherwise misexpress 14815. The cell preparation can consist of human or non-human cells, e.g., rodent cells, e.g., mouse or rat cells, rabbit cells, or pig cells. In preferred embodiments, the cell or cells include a 14815 transgene, e.g., a heterologous form of a 14815, e.g., a gene derived from humans (in the case of a non-human cell). The 14815 transgene can be misexpressed, e.g., overexpressed or underexpressed. In other preferred embodiments, the cell or cells include a gene which misexpresses an endogenous 14815, e.g., a gene the expression of which is disrupted, e.g., a knockout. Such cells can serve as a model for studying disorders which are related to mutated or misexpressed 14815 alleles or for use in drug screening.

In another aspect, the invention features, a human cell, e.g., a hematopoietic stem cell, transformed with nucleic acid which encodes a subject 14815 polypeptide.

Also provided are cells, preferably human cells, e.g., human hematopoietic or fibroblast cells, in which an endogenous 14815 is under the control of a regulatory sequence that does not normally control the expression of the endogenous 14815 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 14815 gene. For example, an endogenous 14815 gene which is "transcriptionally silent," e.g., not normally expressed, or expressed only at very low levels, can be activated by inserting a regulatory element which is capable of promoting the expression of a normally expressed gene product in that cell. Techniques such as targeted homologous recombinations, can be used to insert the heterologous DNA as described in, e.g., Chappel, U.S. Pat. No. 5,272,071; WO 91/06667, published in May 16, 1991.

Transgenic Animals

The invention provides non-human transgenic animals. Such animals are useful for studying the function and/or activity of a 14815 protein and for identifying and/or evaluating modulators of 14815 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 14815 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention in order to direct expression of a 14815 protein to particular cells. A transgenic founder animal can be identified based upon the presence of a 14815 transgene in its genome and/or expression of 14815 mRNA in tissues or cells of the animals. A transgenic founder animal can then be used to breed additional animals carrying the transgene.

Moreover, transgenic animals carrying a transgene encoding a 14815 protein can further be bred to other transgenic animals carrying other transgenes.

14815 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed, e.g., below.

Uses

The nucleic acid molecules, proteins, protein homologs, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 14815 protein (e.g., via a recombinant expression vector in a host cell in gene therapy applications), to detect a 14815 mRNA (e.g., in a biological sample) or a genetic alteration in a 14815 gene, and to modulate 14815 activity, as described further below. The 14815 proteins can be used to treat disorders characterized by insufficient or excessive production of a 14815 substrate or production of 14815 inhibitors. In addition, the 14815 proteins can be used to screen for naturally occurring 14815 substrates, to screen for drugs or compounds which modulate 14815 activity, as well as to treat disorders characterized by insufficient or excessive production of 14815 protein or production of 14815 protein forms which have decreased, aberrant or unwanted activity compared to 14815 wild type protein (e.g., aberrant or deficient kinase function or expression). Moreover, the anti-14815 antibodies of the invention can be used to detect and isolate 14815 proteins, regulate the bioavailability of 14815 proteins, and modulate 14815 activity.

A method of evaluating a compound for the ability to interact with, e.g., bind, a subject 14815 polypeptide is provided. The method includes: contacting the compound with the subject 14815 polypeptide; and evaluating ability of the compound to interact with, e.g., to bind or form a complex with the subject 14815 polypeptide. This method can be performed in vitro, e.g., in a cell free system, or in vivo, e.g., in a two-hybrid interaction trap assay. This method can be used to identify naturally occurring molecules which interact with subject 14815 polypeptide. It can also be used to find natural or synthetic inhibitors of subject 14815 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 14815 proteins, have a stimulatory or inhibitory effect on, for example, 14815 expression or 14815 activity, or have a stimulatory or inhibitory effect on, for example, the expression or activity of a 14815 substrate. Compounds thus identified can be used to modulate the activity of target gene products (e.g., 14815 genes) in a therapeutic protocol, to elaborate the biological function of the target gene product, or to identify compounds that disrupt normal target gene interactions.

In one embodiment, the invention provides assays for screening candidate or test compounds which are substrates of a 14815 protein or polypeptide or a biologically active portion thereof. In another embodiment, the invention provides assays for screening candidate or test compounds which bind to or modulate the activity of a 14815 protein or polypeptide or a biologically active portion thereof.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909–13; Erb et al. (1994) *Proc. Natl. Acad. Sci. USA* 91:11422–426; Zuckermann et al. (1994). *J. Med. Chem.* 37:2678–85; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233–51.

Libraries of compounds can be presented in solution (e.g., Houghten (1992) *Biotechniques* 13:412–421), or on beads (Lam (1991) *Nature* 354:82–84), chips (Fodor (1993) *Nature* 364:555–556), bacteria (Ladner, U.S. Pat. No. 5,223, 409), spores (Ladner USP '409), plasmids (Cull et al. (1992) *Proc Natl Acad Sci USA* 89:1865–1869) or on phage (Scott and Smith (1990) *Science* 249:386–390; Devlin (1990) *Science* 249:404–406; Cwirla et al. (1990) *Proc. Natl. Acad. Sci.* 87:6378–6382; Felici (1991) *J. Mol. Biol.* 222:301–310; Ladner supra.).

In one embodiment, an assay is a cell-based assay in which a cell which expresses a 14815 protein or biologically active portion thereof is contacted with a test compound, and the ability of the test compound to modulate 14815 activity is determined. Determining the ability of the test compound to modulate 14815 activity can be accomplished by monitoring, for example, phosphorylation of a protein, e.g. phosphorylation of a tyrosine residue on a protein, the binding of a nucleotide, e.g. ATP or GTP, to a 14815 polypeptide, or the binding of a 14815 polypeptide to another protein, e.g. another 14815 protein, a different kinase, a cyclin, an ankyrin repeat-containing protein, nucleoplasmin, importin, a ras protein, or vinculin. The cell, for example, can be of mammalian origin, e.g., human.

The ability of the test compound to modulate 14815 binding to a compound, e.g., a 14815 substrate, or to bind to 14815 can also be evaluated. This can be accomplished, for example, by coupling the compound, e.g., the substrate, with a radioisotope or enzymatic label such that binding of the compound, e.g., the substrate, to 14815 can be determined by detecting the labeled compound, e.g., substrate, in a complex. Alternatively, 14815 could be coupled with a radioisotope or enzymatic label to monitor the ability of a test compound to modulate 14815 binding to a 14815 substrate in a complex. For example, compounds (e.g., 14815 substrates) can be labeled with $^{125}$I, $^{14}$C, $^{35}$S or $^{3}$H., either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 14815 substrate) to interact with 14815 with or without the labeling of any of the interactants can be evaluated. For example, a microphysiometer can be used to detect the interaction of a compound with 14815 without the labeling of either the compound or the 14815. McConnell et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 14815.

In yet another embodiment, a cell-free assay is provided in which a 14815 protein or biologically active portion thereof is contacted with a test compound and the ability of the test compound to bind to the 14815 protein or biologically active portion thereof is evaluated. Preferred biologically active portions of the 14815 proteins to be used in assays of the present invention include fragments which participate in interactions with non-14815 molecules, e.g., fragments with high surface probability scores.

Soluble and/or membrane-bound forms of isolated proteins (e.g., 14815 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 14815 protein to bind to a target molecule can be accomplished using real-time Biomolecular Interaction Analysis (BIA) (see, e.g., Sjolander and Urbaniczky (1991) *Anal. Chem.* 63:2338–2345 and Szabo et al. (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 14815, an anti-14815 antibody or its target molecule to facilitate separation of complexed from uncomplexed forms of one or both of the proteins, as well as to accommodate automation of the assay. Binding of a test compound to a 14815 protein, or interaction of a 14815 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/14815 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 14815 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 14815 binding or activity determined using standard techniques.

Other techniques for immobilizing either a 14815 protein or a target molecule on matrices include using conjugation of biotin and streptavidin. Biotinylated 14815 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific or selective for the immobilized component (the antibody, in turn, can be directly labeled or indirectly labeled with, e.g., a labeled anti-Ig antibody).

In one embodiment, this assay is performed utilizing antibodies reactive with 14815 protein or target molecules but which do not interfere with binding of the 14815 protein to its target molecule. Such antibodies can be derivatized to the wells of the plate, and unbound target or 14815 protein trapped in the wells by antibody conjugation. Methods for detecting such complexes, in addition to those described above for the GST-immobilized complexes, include immunodetection of complexes using antibodies reactive with the 14815 protein or target molecule, as well as enzyme-linked assays which rely on detecting an enzymatic activity associated with the 14815 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993) *Trends Biochem Sci* 18:284–7); chromatography (gel filtration chromatography, ion-exchange chromatography); electrophoresis (see, e.g., Ausubel et al., eds. (1999) *Current Protocols in Molecular Biology*, J. Wiley, New York.); and immunoprecipitation (see, for example, Ausubel et al., eds. (1999) *Current Protocols in Molecular Biology*, J. Wiley, New York). Such resins and chromatographic techniques are known to one skilled in the art (see, e.g., Heegaard (1998) *J Mol Recognit* 11:141–8; Hage and Tweed (1997) *J Chromatogr B Biomed Sci Appl.* 699:499–525). Further, fluorescence energy transfer can also be conveniently utilized, as described herein, to detect binding without further purification of the complex from solution.

In a preferred embodiment, the assay includes contacting the 14815 protein or biologically active portion thereof with a known compound which binds 14815 to form an assay mixture, contacting the assay mixture with a test compound, and determining the ability of the test compound to interact with a 14815 protein, wherein determining the ability of the test compound to interact with a 14815 protein includes determining the ability of the test compound to preferentially bind to 14815 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 14815 genes herein identified. In an alternative embodiment, the invention provides methods for determining the ability of the test compound to modulate the activity of a 14815 protein through modulation of the activity of a downstream effector of a 14815 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific or selective for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific or selective for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific or selective for one of the binding components to anchor any complexes formed in solution, and a labeled antibody specific or selective for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 14815 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 14815 ("14815-binding proteins" or "14815-bp") and are involved in 14815 activity. Such 14815-bps can be activators or inhibitors of signals by the 14815 proteins or 14815 targets as, for example, downstream elements of a 14815-mediated signaling pathway.

The two-hybrid system is based on the modular nature of most transcription factors, which consist of separable DNA-binding and activation domains. Briefly, the assay utilizes two different DNA constructs. In one construct, the gene that codes for a 14815 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 14815 protein can be the fused to the activator domain.) If the "bait" and the "prey" proteins are able to interact, in vivo, forming a 14815-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 14815 protein.

In another embodiment, modulators of 14815 expression are identified. For example, a cell or cell free mixture is contacted with a candidate compound and the expression of 14815 mRNA or protein evaluated relative to the level of expression of 14815 mRNA or protein in the absence of the candidate compound. When expression of 14815 mRNA or protein is greater in the presence of the candidate compound than in its absence, the candidate compound is identified as a stimulator of 14815 mRNA or protein expression. Alternatively, when expression of 14815 mRNA or protein is less (statistically significantly less) in the presence of the candidate compound than in its absence, the candidate compound is identified as an inhibitor of 14815 mRNA or protein expression. The level of 14815 mRNA or protein expression can be determined by methods described herein for detecting 14815 mRNA or protein.

In another aspect, the invention pertains to a combination of two or more of the assays described herein. For example, a modulating agent can be identified using a cell-based or a cell free assay, and the ability of the agent to modulate the activity of a 14815 protein can be confirmed in vivo, e.g., in an animal such as an animal model for aberrant or deficient kinase function or expression.

This invention further pertains to novel agents identified by the above-described screening assays. Accordingly, it is within the scope of this invention to further use an agent identified as described herein (e.g., a 14815 modulating agent, an antisense 14815 nucleic acid molecule, a 14815-specific antibody, or a 14815-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 14815 with a disease; (ii) identify an individual from a minute biological sample (tissue typing); and (iii) aid in forensic identification of a biological sample. These applications are described in the subsections below.

Chromosome Mapping

The 14815 nucleotide sequences or portions thereof can be used to map the location of the 14815 genes on a chromosome. This process is called chromosome mapping. Chromosome mapping is useful in correlating the 14815 sequences with genes associated with disease.

Briefly, 14815 genes can be mapped to chromosomes by preparing PCR primers (preferably 15–25 bp in length) from the 14815 nucleotide sequences. These primers can then be used for PCR screening of somatic cell hybrids containing individual human chromosomes. Only those hybrids containing the human gene corresponding to the 14815 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919–924).

Other mapping strategies e.g., in situ hybridization (described in Fan et al. (1990) *Proc. Natl. Acad. Sci. USA*, 87:6223–27), pre-screening with labeled flow-sorted chromosomes, and pre-selection by hybridization to chromosome specific cDNA libraries can be used to map 14815 to a chromosomal location.

Fluorescence in situ hybridization (FISH) of a DNA sequence to a metaphase chromosomal spread can further be used to provide a precise chromosomal location in one step.

The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. (1988) Human Chromosomes: A Manual of Basic Techniques, Pergamon Press, New York).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in McKusick, *Mendelian Inheritance in Man*, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature,* 325:783–787.

Moreover, differences in the DNA sequences between individuals affected and unaffected with a disease associated with the 14815 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 14815 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 14815 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 14815 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 14815 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 14815 nucleotide sequences described herein can further be used to provide polynucleotide reagents, e.g., labeled or labelable probes which can be used in, for example, an in situ hybridization technique, to identify a specific tissue. This can be very useful in cases where a forensic pathologist is presented with a tissue of unknown origin. Panels of such 14815 probes can be used to identify tissue by species and/or by organ type.

In a similar fashion, these reagents, e.g., 14815 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 14815.

Such disorders include, e.g., a disorder associated with the misexpression of 14815 gene; a disorder of the cellular proliferative and/or differentiative system, cell signaling system or nervous system.

The method includes one or more of the following:

detecting, in a tissue of the subject, the presence or absence of a mutation which affects the expression of the 14815 gene, or detecting the presence or absence of a mutation in a region which controls the expression of the gene, e.g., a mutation in the 5' control region;

detecting, in a tissue of the subject, the presence or absence of a mutation which alters the structure of the 14815 gene;

detecting, in a tissue of the subject, the misexpression of the 14815 gene, at the mRNA level, e.g., detecting a non-wild type level of an mRNA;

detecting, in a tissue of the subject, the misexpression of the gene, at the protein level, e.g., detecting a non-wild type level of a 14815 polypeptide.

In preferred embodiments the method includes: ascertaining the existence of at least one of: a deletion of one or more nucleotides from the 14815 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1, or naturally occurring mutants thereof or 5' or 3' flanking sequences naturally associated with the 14815 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 14815 gene; the presence of a non-wild type splicing pattern of a messenger RNA transcript of the gene; or a non-wild type level of 14815.

Methods of the invention can be used prenatally or to determine if a subject's offspring will be at risk for a disorder.

In preferred embodiments the method includes determining the structure of a 14815 gene, an abnormal structure being indicative of risk for the disorder.

In preferred embodiments the method includes contacting a sample from the subject with an antibody to the 14815 protein or a nucleic acid, which hybridizes specifically with the gene. These and other embodiments are discussed below.

Diagnostic and Prognostic Assays

The presence, level, or absence of 14815 protein or nucleic acid in a biological sample can be evaluated by obtaining a biological sample from a test subject and contacting the biological sample with a compound or an agent capable of detecting 14815 protein or nucleic acid (e.g., mRNA, genomic DNA) that encodes 14815 protein such that the presence of 14815 protein or nucleic acid is detected in the biological sample. The term "biological sample" includes tissues, cells and biological fluids isolated from a subject, as well as tissues, cells and fluids present within a subject. A preferred biological sample is serum. The level of expression of the 14815 gene can be measured in a number of ways, including, but not limited to: measuring the mRNA encoded by the 14815 genes; measuring the amount of protein encoded by the 14815 genes; or measuring the activity of the protein encoded by the 14815 genes.

The level of mRNA corresponding to the 14815 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 14815 nucleic acid, such as the nucleic acid of SEQ ID NO:1, or a portion thereof, such as an oligonucleotide of at least 7, 15, 30, 50, 100, 250 or 500 nucleotides in length and sufficient to specifically hybridize under stringent conditions to 14815 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 14815 genes.

The level of mRNA in a sample that is encoded by one of 14815 can be evaluated with nucleic acid amplification, e.g., by rtPCR (Mullis (1987) U.S. Pat. No. 4,683,202), ligase chain reaction (Barany (1991) *Proc. Natl. Acad. Sci. USA* 88:189–193), self sustained sequence replication (Guatelli et al., (1990) *Proc. Natl. Acad. Sci. USA* 87:1874–1878), transcriptional amplification system (Kwoh et al., (1989), *Proc. Natl. Acad. Sci. USA* 86:1173–1177), Q-Beta Replicase (Lizardi et al., (1988) *Bio/Technology* 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 14815 gene being analyzed.

In another embodiment, the methods further contacting a control sample with a compound or agent capable of detecting 14815 mRNA, or genomic DNA, and comparing the presence of 14815 mRNA or genomic DNA in the control sample with the presence of 14815 mRNA or genomic DNA in the test sample.

A variety of methods can be used to determine the level of protein encoded by 14815. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 14815 protein in a biological sample in vitro as well as in vivo. In vitro techniques for detection of 14815 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 14815 protein include introducing into a subject a labeled anti-14815 antibody. For example, the antibody can be labeled with a radioactive marker whose presence and location in a subject can be detected by standard imaging techniques.

In another embodiment, the methods further include contacting the control sample with a compound or agent capable of detecting 14815 protein, and comparing the presence of 14815 protein in the control sample with the presence of 14815 protein in the test sample.

The invention also includes kits for detecting the presence of 14815 in a biological sample. For example, the kit can include a compound or agent capable of detecting 14815 protein or mRNA in a biological sample; and a standard. The compound or agent can be packaged in a suitable container. The kit can further comprise instructions for using the kit to detect 14815 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 14815 expression or activity. As used herein, the term "unwanted" includes an unwanted phenomenon involved in a biological response such as pain or deregulated cell proliferation.

In one embodiment, a disease or disorder associated with aberrant or unwanted 14815 expression or activity is identified. A test sample is obtained from a subject and 14815 protein or nucleic acid (e.g., mRNA or genomic DNA) is evaluated, wherein the level, e.g., the presence or absence, of 14815 protein or nucleic acid is diagnostic for a subject having or at risk of developing a disease or disorder associated with aberrant or unwanted 14815 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 14815 expression or activity. For example, such methods can be used to determine whether a subject can be effectively treated with an agent for a cellular proliferative and/or differentiative disorder, neurological disorder, liver disorder, apoptotic disorder, metabolic disorder or hormonal disorder.

The methods of the invention can also be used to detect genetic alterations in a 14815 gene, thereby determining if a subject with the altered gene is at risk for a disorder characterized by misregulation in 14815 protein activity or nucleic acid expression, such as a cellular proliferative and/or differentiative disorder, neurological disorder, liver disorder, apoptotic disorder, metabolic disorder or hormonal disorder. In preferred embodiments, the methods include detecting, in a sample from the subject, the presence or absence of a genetic alteration characterized by at least one of an alteration affecting the integrity of a gene encoding a 14815-protein, or the mis-expression of the 14815 gene. For example, such genetic alterations can be detected by ascertaining the existence of at least one of 1) a deletion of one or more nucleotides from a 14815 gene; 2) an addition of one or more nucleotides to a 14815 gene; 3) a substitution of one or more nucleotides of a 14815 gene, 4) a chromosomal rearrangement of a 14815 gene; 5) an alteration in the level of a messenger RNA transcript of a 14815 gene, 6) aberrant modification of a 14815 gene, such as of the methylation pattern of the genomic DNA, 7) the presence of a non-wild type splicing pattern of a messenger RNA transcript of a 14815 gene, 8) a non-wild type level of a 14815-protein, 9) allelic loss of a 14815 gene, and 10) inappropriate post-translational modification of a 14815-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 14815-gene. This method can include the steps of collecting a sample of cells from a subject, isolating nucleic acid (e.g., genomic, mRNA or both) from the sample, contacting the nucleic acid sample with one or more primers which specifically hybridize to a 14815 gene under conditions such that hybridization and amplification of the 14815 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein. Alternatively, other amplification methods described herein or known in the art can be used.

In another embodiment, mutations in a 14815 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 14815 can be identified by hybridizing a sample and control nucleic acids, e.g., DNA or RNA, two dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. (1996) *Human Mutation* 7: 244–255; Kozal et al. (1996) *Nature Medicine* 2: 753–759). For example, genetic mutations in 14815 can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 14815 gene and detect mutations by comparing the sequence of the sample 14815 with the corresponding wild-type (control) sequence. Automated sequencing procedures can be utilized when performing the diagnostic assays (Naeve et al. (1995) *Biotechniques* 19:448–53), including sequencing by mass spectrometry.

Other methods for detecting mutations in the 14815 gene include methods in which protection from cleavage agents is used to detect mismatched bases in RNA/RNA or RNA/DNA heteroduplexes (Myers et al. (1985) *Science* 230:1242; Cotton et al. (1988) *Proc. Natl Acad Sci USA* 85:4397; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 14815 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 14815 genes. For example, single strand conformation polymorphism (SSCP) can be used to detect differences in electrophoretic mobility between mutant and wild type nucleic acids (Orita et al. (1989) *Proc Natl. Acad. Sci USA:* 86:2766, see also Cotton (1993) *Mutat. Res.* 285:125–144; and Hayashi (1992) *Genet. Anal. Tech. Appl.* 9:73–79). Single-stranded DNA fragments of sample and control 14815 nucleic acids will be denatured and allowed to renature. The secondary structure of single-stranded nucleic acids varies according to sequence, the resulting alteration in electrophoretic mobility enables the detection of even a single base change. The DNA fragments can be labeled or detected with labeled probes. The sensitivity of the assay can be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl Acad. Sci USA* 86:6230).

Alternatively, allele specific amplification technology which depends on selective PCR amplification can be used in conjunction with the instant invention. Oligonucleotides used as primers for specific amplification can carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification can also be performed using Taq ligase for amplification (Barany (1991) *Proc. Natl. Acad. Sci USA* 88:189–93). In such cases, ligation will occur only if there is a perfect match at the 3' end of the 5' sequence making it possible to detect the presence of a known mutation at a specific site by looking for the presence or absence of amplification.

The methods described herein can be performed, for example, by utilizing pre-packaged diagnostic kits comprising at least one probe nucleic acid or antibody reagent described herein, which can be conveniently used, e.g., in clinical settings to diagnose patients exhibiting symptoms or family history of a disease or illness involving a 14815 gene.

Use of 14815 Molecules as Surrogate Markers

The 14815 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 14815 molecules of the invention can be detected, and can be correlated with one or more biological states in vivo. For example, the 14815 molecules of the invention can serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers can serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease can be made using cholesterol levels as a surrogate marker, and an analysis of HIV infection can be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 14815 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker can be indicative of the concentration of the drug in a biological tissue, in that the marker is either expressed or transcribed or not expressed or transcribed in that tissue in relationship to the level of the drug. In this fashion, the distribution or uptake of the drug can be monitored by the pharmacodynamic marker. Similarly, the presence or quantity of the pharmacodynamic marker can be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug can be sufficient to activate multiple rounds of marker (e.g., a 14815 marker) transcription or expression, the amplified marker can be in a quantity which is more readily detectable than the drug itself. Also, the marker can be more easily detected due to the nature of the marker itself; for example, using the methods described herein, anti-14815 antibodies can be employed in an immune-based detection system for a 14815 protein marker, or 14815-specific radiolabeled probes can be used to detect a 14815 mRNA marker. Furthermore, the use of a pharmacodynamic marker can offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am. J. Health-Syst. Pharm.* 56 Suppl. 3: S16–S20.

The 14815 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35:1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, can be selected. For example, based on the presence or quantity of RNA, or protein (e.g., 14815 protein or RNA) for specific tumor markers in a subject, a drug or course of treatment can be selected that is optimized for the treatment of the specific tumor likely to be present in the subject. Similarly, the presence or absence of a specific sequence mutation in 14815 DNA can correlate with a 14815 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-14815 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral, transdermal (e.g. topical), transmucosal (e.g., inhalation of aerosol or absorption of eye drop), and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about I to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody, unconjugated or conjugated as described herein, can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent can, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having a disorder associated with aberrant or unwanted 14815 expression or activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

With regards to both prophylactic and therapeutic methods of treatment, such treatments can be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 14815 molecules of the present invention or 14815 modulators according to that individual's drug response genotype. Pharmacogenomics allows a clinician or physician to target prophylactic or therapeutic treatments to patients who will most benefit from the treatment and not to provide this treatment to patients who will experience toxic drug-related side effects.

In one aspect, the invention provides a method for preventing in a subject, a disease or condition associated with an aberrant or unwanted 14815 expression or activity, by administering to the subject a 14815 or an agent which modulates 14815 expression or at least one 14815 activity. Subjects at risk for a disease which is caused or contributed to by aberrant or unwanted 14815 expression or activity can be identified by, for example, any or a combination of diagnostic or prognostic assays as described herein. Administration of a prophylactic agent can occur prior to the manifestation of symptoms characteristic of the 14815 aberrance, such that a disease or disorder is prevented or, alternatively, delayed in its progression. Depending on the type of 14815 aberrance, for example, a 14815, 14815 agonist or 14815 antagonist agent can be used for treating the subject. The appropriate agent can be determined based on screening assays described herein.

It is possible that some 14815 disorders can be caused, at least in part, by an abnormal level of gene product, or by the presence of a gene product exhibiting abnormal activity. As such, the reduction in the level and/or activity of such gene products would bring about the amelioration of disorder symptoms.

The 14815 molecules can act as novel diagnostic targets and therapeutic agents for controlling one or more of neurological disorders, hepatic disorders, cellular proliferative and/or differentiative disorders, inflammatory disorders, apoptotic disorders, metabolic disorders and hormonal disorders, all of which are described above.

As discussed, successful treatment of 14815 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 14815 disorders. Such molecules can include, but are not limited to peptides, phosphopeptides, small organic or inorganic molecules, or antibodies (including, for example, polyclonal, monoclonal, humanized, human, anti-idiotypic, chimeric or single chain antibodies, and Fab, $F(ab')_2$ and Fab expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules can be utilized in treating or preventing a disease characterized by 14815 expression is through the use of aptamer molecules specific for 14815 protein. Aptamers are nucleic acid molecules having a tertiary structure which permits them to specifically or selectively bind to protein ligands (see, e.g., Osborne et al. (1997) *Curr. Opin. Chem Biol.* 1: 5–9; and Patel (1997) *Curr Opin Chem Biol* 1:32–46). Since nucleic acid molecules can in many cases be more conveniently introduced into target cells than therapeutic protein molecules can be, aptamers offer a method by which 14815 protein activity can be specifically decreased without the introduction of drugs or other molecules which can have pluripotent effects.

Antibodies can be generated that are both specific for target gene product and that reduce target gene product activity. Such antibodies can, therefore, by administered in instances whereby negative modulatory techniques are appropriate for the treatment of 14815 disorders. For a description of antibodies, see the Antibody section above.

In circumstances wherein injection of an animal or a human subject with a 14815 protein or epitope for stimulating antibody production is harmful to the subject, it is possible to generate an immune response against 14815 through the use of anti-idiotypic antibodies (see, for example, Herlyn (1999) *Ann Med* 31:66–78; and Bhattacharya-Chatterjee and Foon (1998) *Cancer Treat Res.* 94:51–68). If an anti-idiotypic antibody is introduced into a mammal or human subject, it should stimulate the production of anti-anti-idiotypic antibodies, which should be specific to the 14815 protein. Vaccines directed to a disease characterized by 14815 expression can also be generated in this fashion.

In instances where the target antigen is intracellular and whole antibodies are used, internalizing antibodies can be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 14815 disorders. A therapeutically effective dose refers to that amount of the compound sufficient to result in amelioration of symptoms of the disorders. Toxicity and therapeutic efficacy of such compounds can be determined by standard pharmaceutical procedures as described above.

The data obtained from the cell culture assays and animal studies can be used in formulating a range of dosage for use in humans. The dosage of such compounds lies, preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to modulate 14815 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al (1996) *Current Opinion in Biotechnology* 7:89–94 and in Shea (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al (1993) *Nature* 361:645–647. Through the use of isotope-labeling, the "free" concentration of compound which modulates the expression or activity of 14815 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. An rudimentary example of such a "biosensor" is discussed in Kriz et al (1995) *Analytical Chemistry* 67:2142–2144.

Another aspect of the invention pertains to methods of modulating 14815 expression or activity for therapeutic purposes. Accordingly, in an exemplary embodiment, the modulatory method of the invention involves contacting a cell with a 14815 or agent that modulates one or more of the activities of 14815 protein activity associated with the cell. An agent that modulates 14815 protein activity can be an agent as described herein, such as a nucleic acid or a protein, a naturally-occurring target molecule of a 14815 protein (e.g., a 14815 substrate or receptor), a 14815 antibody, a 14815 agonist or antagonist, a peptidomimetic of a 14815 agonist or antagonist, or other small molecule.

In one embodiment, the agent stimulates one or 14815 activities. Examples of such stimulatory agents include active 14815 protein and a nucleic acid molecule encoding 14815. In another embodiment, the agent inhibits one or more 14815 activities. Examples of such inhibitory agents include antisense 14815 nucleic acid molecules, anti-14815 antibodies, and 14815 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 14815 protein or nucleic acid molecule. In one embodiment, the method involves administering an agent (e.g., an agent identified by a screening assay described herein), or combination of agents that modulates (e.g., up regulates or down regulates) 14815 expression or activity. In another embodiment, the method involves administering a 14815 protein or nucleic acid molecule as therapy to compensate for reduced, aberrant, or unwanted 14815 expression or activity.

Stimulation of 14815 activity is desirable in situations in which 14815 is abnormally downregulated and/or in which increased 14815 activity is likely to have a beneficial effect. For example, stimulation of 14815 activity is desirable in situations in which a 14815 is downregulated and/or in which increased 14815 activity is likely to have a beneficial effect. Likewise, inhibition of 14815 activity is desirable in situations in which 14815 is abnormally upregulated and/or in which decreased 14815 activity is likely to have a beneficial effect.

Pharmacogenomics

The 14815 molecules of the present invention, as well as agents, or modulators which have a stimulatory or inhibitory effect on 14815 activity (e.g., 14815 gene expression) as identified by a screening assay described herein can be administered to individuals to treat (prophylactically or therapeutically) 14815-associated disorders (e.g., aberrant or deficient kinase function or expression) associated with aberrant or unwanted 14815 activity. In conjunction with such treatment, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a 14815 molecule or 14815 modulator as well as tailoring the dosage and/or therapeutic regimen of treatment with a 14815 molecule or 14815 modulator.

Pharmacogenomics deals with clinically significant hereditary variations in the response to drugs due to altered drug disposition and abnormal action in affected persons. See, for example, Eichelbaum et al. (1996) *Clin. Exp. Pharmacol. Physiol.* 23:983–985 and Linder et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP can occur once per every 1000 bases of DNA. A SNP can be involved in a disease process, however, the vast majority can not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that can be common among such genetically similar individuals.

Alternatively, a method termed the "candidate gene approach", can be utilized to identify genes that predict drug response. According to this method, if a gene that encodes a drug's target is known (e.g., a 14815 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 14815 molecule or 14815 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 14815 molecule or 14815 modulator, such as a modulator identified by one of the exemplary screening assays described herein.

The present invention further provides methods for identifying new agents, or combinations, that are based on identifying agents that modulate the activity of one or more of the gene products encoded by one or more of the 14815 genes of the present invention, wherein these products can be associated with resistance of the cells to a therapeutic agent. Specifically, the activity of the proteins encoded by the 14815 genes of the present invention can be used as a basis for identifying agents for overcoming agent resistance. By blocking the activity of one or more of the resistance proteins, target cells, e.g., human cells, will become sensitive to treatment with an agent to which the unmodified target cells were resistant.

Monitoring the influence of agents (e.g., drugs) on the expression or activity of a 14815 protein can be applied in clinical trials. For example, the effectiveness of an agent determined by a screening assay as described herein to increase 14815 gene expression, protein levels, or upregulate 14815 activity, can be monitored in clinical trials of subjects exhibiting decreased 14815 gene expression, protein levels, or downregulated 14815 activity. Alternatively, the effectiveness of an agent determined by a screening assay to decrease 14815 gene expression, protein levels, or downregulate 14815 activity, can be monitored in clinical trials of subjects exhibiting increased 14815 gene expression, protein levels, or upregulated 14815 activity. In such clinical trials, the expression or activity of a 14815 gene, and preferably, other genes that have been implicated in, for example, a kinase-associated or another 14815-associated disorder can be used as a "read out" or markers of the phenotype of a particular cell.

Other Embodiments

In another aspect, the invention features a method of analyzing a plurality of capture probes. The method is useful, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence, wherein the capture probes are from a cell or subject which expresses 14815 or from a cell or subject in which a 14815 mediated response has been elicited; contacting the array with a 14815 nucleic acid (preferably purified), a 14815 polypeptide (preferably purified), or an anti-14815 antibody, and thereby evaluating the plurality of capture probes. Binding, e.g., in the case of a nucleic acid, hybridization with a capture probe at an address of the plurality, is detected, e.g., by a signal generated from a label attached to the 14815 nucleic acid, polypeptide, or antibody.

The capture probes can be a set of nucleic acids from a selected sample, e.g., a sample of nucleic acids derived from a control or non-stimulated tissue or cell.

The method can include contacting the 14815 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 14815. Such methods can be used to diagnose a subject, e.g., to evaluate risk for a disease or disorder, to evaluate suitability of a selected treatment for a subject, to evaluate whether a subject has a disease or disorder.

The method can be used to detect SNPs, as described above.

In another aspect, the invention features a method of analyzing 14815, e.g., analyzing structure, function, or relatedness to other nucleic acid or amino acid sequences. The method includes: providing a 14815 nucleic acid or amino acid sequence; comparing the 14815 sequence with one or more preferably a plurality of sequences from a collection of sequences, e.g., a nucleic acid or protein sequence database; to thereby analyze 14815.

The method can include evaluating the sequence identity between a 14815 sequence and a database sequence. The method can be performed by accessing the database at a second site, e.g., over the internet. Preferred databases include GenBank™ and SwissProt.

In another aspect, the invention features, a set of oligonucleotides, useful, e.g., for identifying SNP's, or identifying specific alleles of 14815. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with differential labels, such that an oligonucleotide which hybridizes to one allele provides a signal that is distinguishable from an oligonucleotides which hybridizes to a second allele.

The sequences of 14815 molecules are provided in a variety of mediums to facilitate use thereof. A sequence can be provided as a manufacture, other than an isolated nucleic acid or amino acid molecule, which contains a 14815 molecule. Such a manufacture can provide a nucleotide or amino acid sequence, e.g., an open reading frame, in a form which allows examination of the manufacture using means not directly applicable to examining the nucleotide or amino acid sequences, or a subset thereof, as they exist in nature or in purified form.

A 14815 nucleotide or amino acid sequence can be recorded on computer readable media. As used herein, "computer readable media" refers to any medium that can be read and accessed directly by a computer. Such media include, but are not limited to: magnetic storage media, such as floppy discs, hard disc storage medium, and magnetic tape; optical storage media such as compact disc and CD-ROM; electrical storage media such as RAM, ROM, EPROM, EEPROM, and the like; and general hard disks and hybrids of these categories such as magnetic/optical storage media. The medium is adapted or configured for having thereon 14815 sequence information of the present invention.

As used herein, the term "electronic apparatus" is intended to include any suitable computing or processing apparatus of other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as personal digital assistants (PDAs), cellular phones, pagers, and the like; and local and distributed processing systems.

As used herein, "recorded" refers to a process for storing or encoding information on the electronic apparatus readable medium. Those skilled in the art can readily adopt any of the presently known methods for recording information on known media to generate manufactures comprising the 14815 sequence information.

A variety of data storage structures are available to a skilled artisan for creating a computer readable medium having recorded thereon a 14815 nucleotide or amino acid sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. The skilled artisan can readily adapt any number of data processor structuring formats (e.g., text file or database) in order to obtain computer readable medium having recorded thereon the nucleotide sequence information of the present invention.

By providing the 14815 nucleotide or amino acid sequences of the invention in computer readable form, the skilled artisan can routinely access the sequence information for a variety of purposes. For example, one skilled in the art can use the nucleotide or amino acid sequences of the invention in computer readable form to compare a target sequence or target structural motif with the sequence information stored within the data storage means. A search is used to identify fragments or regions of the sequences of the invention which match a particular target sequence or target motif.

The present invention therefore provides a medium for holding instructions for performing a method for determining whether a subject has a kinase-associated or another 14815-associated disease or disorder or a pre-disposition to a kinase-associated or another 14815-associated disease or disorder, wherein the method comprises the steps of determining 14815 sequence information associated with the subject and based on the 14815 sequence information, determining whether the subject has a kinase-associated or another 14815-associated disease or disorder and/or recommending a particular treatment for the disease, disorder, or pre-disease condition.

The present invention further provides in an electronic system and/or in a network, a method for determining whether a subject has a kinase-associated or another 14815-associated disease or disorder or a pre-disposition to a disease associated with 14815, wherein the method comprises the steps of determining 14815 sequence information associated with the subject, and based on the 14815 sequence information, determining whether the subject has a kinase-associated or another 14815-associated disease or disorder or a pre-disposition to a kinase-associated or another 14815-associated disease or disorder, and/or recommending a particular treatment for the disease, disorder, or pre-disease condition. The method may further comprise the step of receiving phenotypic information associated with the subject and/or acquiring from a network phenotypic information associated with the subject.

The present invention also provides in a network, a method for determining whether a subject has a kinase-associated or another 14815-associated disease or disorder or a pre-disposition to a kinase-associated or another 14815-associated disease or disorder, said method comprising the steps of receiving 14815 sequence information from the subject and/or information related thereto, receiving phenotypic information associated with the subject, acquiring information from the network corresponding to 14815 and/or corresponding to a kinase-associated or another 14815-associated disease or disorder, and based on one or more of the phenotypic information, the 14815 information (e.g., sequence information and/or information related thereto), and the acquired information, determining whether the subject has a kinase-associated or another 14815-associated disease or disorder or a pre-disposition to a kinase-associated or another 14815-associated disease or disorder. The method may further comprise the step of recommending a particular treatment for the disease, disorder, or pre-disease condition.

The present invention also provides a business method for determining whether a subject has a kinase-associated or another 14815-associated disease or disorder or a pre-disposition to a kinase-associated or another 14815-associated disease or disorder, said method comprising the steps of receiving information related to 14815 (e.g., sequence information and/or information related thereto), receiving phenotypic information associated with the subject, acquiring information from the network related to 14815 and/or related to a kinase-associated or another 14815-associated disease or disorder, and based on one or more of the phenotypic information, the 14815 information, and the acquired information, determining whether the subject has a kinase-associated or another 14815-associated disease or disorder or a pre-disposition to a kinase-associated or another 14815-associated disease or disorder. The method may further comprise the step of recommending a particular treatment for the disease, disorder, or pre-disease condition.

The invention also includes an array comprising a 14815 sequence of the present invention. The array can be used to assay expression of one or more genes in the array. In one embodiment, the array can be used to assay gene expression in a tissue to ascertain tissue specificity of genes in the array. In this manner, up to about 7600 genes can be simultaneously assayed for expression, one of which can be 14815. This allows a profile to be developed showing a battery of genes specifically expressed in one or more tissues.

In addition to such qualitative information, the invention allows the quantitation of gene expression. Thus, not only tissue specificity, but also the level of expression of a battery of genes in the tissue if ascertainable. Thus, genes can be grouped on the basis of their tissue expression per se and level of expression in that tissue. This is useful, for example, in ascertaining the relationship of gene expression in that tissue. Thus, one tissue can be perturbed and the effect on gene expression in a second tissue can be determined. In this context, the effect of one cell type on another cell type in response to a biological stimulus can be determined. In this context, the effect of one cell type on another cell type in response to a biological stimulus can be determined. Such a determination is useful, for example, to know the effect of cell—cell interaction at the level of gene expression. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor the time course of expression of one or more genes in the array. This can occur in various biological contexts, as disclosed herein, for example development of a kinase-associated or another 14815-associated disease or disorder, progression of kinase-associated or another 14815-associated disease or disorder, and processes, such a cellular transformation associated with the kinase-associated or another 14815-associated disease or disorder.

The array is also useful for ascertaining the effect of the expression of a gene on the expression of other genes in the same cell or in different cells (e.g., acertaining the effect of 14815 expression on the expression of other genes). This provides, for example, for a selection of alternate molecular targets for therapeutic intervention if the ultimate or downstream target cannot be regulated.

The array is also useful for ascertaining differential expression patterns of one or more genes in normal and abnormal cells. This provides a battery of genes (e.g., including 14815) that could serve as a molecular target for diagnosis or therapeutic intervention.

As used herein, a "target sequence" can be any DNA or amino acid sequence of six or more nucleotides or two or more amino acids. A skilled artisan can readily recognize that the longer a target sequence is, the less likely a target sequence will be present as a random occurrence in the database. Typical sequence lengths of a target sequence are from about 10 to 100 amino acids or from about 30 to 300 nucleotide residues. However, it is well recognized that commercially important fragments, such as sequence fragments involved in gene expression and protein processing, may be of shorter length.

Computer software is publicly available which allows a skilled artisan to access sequence information provided in a computer readable medium for analysis and comparison to other sequences. A variety of known algorithms are disclosed publicly and a variety of commercially available software for conducting search means are and can be used in the computer-based systems of the present invention. Examples of such software include, but are not limited to, MacPattern (EMBL), BLASTN and BLASTX (NCBI).

Thus, the invention features a method of making a computer readable record of a sequence of a 14815 sequence which includes recording the sequence on a computer readable matrix. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

In another aspect, the invention features a method of analyzing a sequence. The method includes: providing a 14815 sequence, or record, in computer readable form; comparing a second sequence to the 14815 sequence; thereby analyzing a sequence. Comparison can include comparing to sequences for sequence identity or determining if one sequence is included within the other, e.g., determining if the 14815 sequence includes a sequence being compared. In a preferred embodiment the 14815 or second sequence is stored on a first computer, e.g., at a first site and the comparison is performed, read, or recorded on a second computer, e.g., at a second site. E.g., the 14815 or second sequence can be stored in a public or proprietary database in one computer, and the results of the comparison performed, read, or recorded on a second computer. In a preferred embodiment the record includes one or more of the following: identification of an ORF; identification of a domain, region, or site; identification of the start of transcription; identification of the transcription terminator; the full length amino acid sequence of the protein, or a mature form thereof; the 5' end of the translated region.

This invention is further illustrated by the following exemplification, which should not be construed as limiting.

EXEMPLIFICATION

Gene Expression Analysis

Total RNA was prepared from various human tissues by a single step extraction method using RNA STAT-60 according to the manufacturer's instructions (TelTest, Inc). Each RNA preparation was treated with DNase I (Ambion) at 37° C. for 1 hour. DNAse I treatment was determined to be complete if the sample required at least 38 PCR amplification cycles to reach a threshold level of fluorescence using β-2 microglobulin as an internal amplicon reference. The integrity of the RNA samples following DNase I treatment was confirmed by agarose gel electrophoresis and ethidium bromide staining. After phenol extraction cDNA was prepared from the sample using the SUPERSCRIPT™ Choice System following the manufacturer's instructions (GibcoBRL). A negative control of RNA without reverse transcriptase was mock reverse transcribed for each RNA sample.

Human 14815 expression was measured by TaqMan® quantitative PCR (Perkin Elmer Applied Biosystems) in cDNA prepared from a variety of normal and diseased (e.g., cancerous) human tissues or cell lines.

Probes were designed by PrimerExpress software (PE Biosystems) based on the sequence of the human 14815 gene. Each human 14815 gene probe was labeled using FAM (6-carboxyfluorescein), and the β2-microglobulin reference probe was labeled with a different fluorescent dye, VIC. The differential labeling of the target gene and internal reference gene thus enabled measurement in same well. Forward and reverse primers and the probes for both β2-microglobulin and target gene were added to the TaqMan® Universal PCR Master Mix (PE Applied Biosystems). Although the final concentration of primer and probe could vary, each was internally consistent within a given experiment. A typical experiment contained 200 nM of forward and reverse primers plus 100 nM probe for β-2 microglobulin and 600 nM forward and reverse primers plus 200 nM probe for the target gene. TaqMan matrix experiments were carried out on an ABI PRISM 7700 Sequence Detection System (PE Applied Biosystems). The sequences of the reagents used to identify 14815 expression included a forward primer, AAGACTGGGCTGAGTTTGTGAAG, SEQ ID NO:10; a reverse primer, CCAAGGGATTGCCTACAAACA, SEQ ID NO:11, and a probe, AACTGCCATGCCTCGAAGACCTGG, SEQ ID NO:12. The thermal cycler conditions were as follows: hold for 2 min at 50° C. and 10 min at 95° C., followed by two-step PCR for 40 cycles of 95° C. for 15 sec followed by 60° C. for 1 min.

The following method was used to quantitatively calculate human 14815 gene expression in the various tissues relative to β-2 microglobulin expression in the same tissue. The threshold cycle (Ct) value is defined as the cycle at which a statistically significant increase in fluorescence is detected. A lower Ct value is indicative of a higher mRNA concentration. The Ct value of the human 14815 gene is normalized by subtracting the Ct value of the β-2 microglobulin gene to obtain a $_\Delta$Ct value using the following formula: $_\Delta Ct = Ct_{human\ 59914\ and\ 59921} - Ct_{\beta-2}$.microglobulin Expression is then calibrated against a cDNA sample showing a comparatively low level of expression of the human 14815 gene. The $_\Delta$Ct value for the calibrator sample is then subtracted from $_\Delta$Ct for each tissue sample according to the following formula: $_{\Delta\Delta}Ct =\ _\Delta Ct\text{-}_{sample} -\ _\Delta Ct\text{-}_{calibrator}$. Relative expression is then calculated using the arithmetic formula given by $2^{-\Delta\Delta Ct}$. Expression of the target human 14815 gene in each of the tissues tested is then graphically represented as discussed in more detail below.

The results indicate significant 14815 expression in normal brain, normal liver and in breast tissue and primary breast tumors, but much less in metastases from the primary tumor.

Expression analysis surveys have found 14815 expression in immune system cells and tissues and have studied changes in 14815 expression in cells and tissues typically involved in inflammatory disorders. The results indicate that certain resting lymphocytes have higher 14815 expression than receptor-stimulated lymphocytes. For example, 14815 expression in resting CD8+ lymphocytes is eight-fold higher than in CD8+ lymphocytes stimulated with anti-CD3 antibodies. In another example, 14815 expression in resting normal human lung fibroblasts is three- to five-fold higher than in normal human lung fibroblasts stimulated with transforming growth factor beta or tumor necrosis factor alpha. In another example, 14815 expression in resting normal human dermal fibroblasts is two- to three-fold higher than in normal human dermal fibroblasts stimulated with transforming growth factor beta or interleukin-1b. In another example, 14815 expression in resting fibroblast-like synoviocytes is two-fold higher than in fibroblast-like synoviocytes stimulated with tumor necrosis factor alpha or interleukin-1. In another example, 14815 expression is two-fold higher in resting normal human bronchial epithelial cells compared with interleukin-4- or interleukin-13-stimulated normal human bronchial epithelial cells. In a further example, 14815 expression in resting bronchial smooth muscle cells is higher than in bronchial smooth muscle cells stimulated with tumor necrosis factor alpha or interferon gamma.

The contents of all references, patents and published patent applications cited throughout this application are incorporated herein by reference.

Equivalents

Those skilled in the art will recognize, or be able to ascertain using no more than routine experimentation, many equivalents to the specific embodiments of the invention described herein.

What is claimed is:

1. An isolated nucleic acid molecule selected from the group consisting of:
   a) a nucleic acid molecule comprising a nucleotide sequence of SEQ ID NO:1 or SEQ ID NO:3;
   b) a nucleic acid molecule which encodes a polypeptide comprising the amino acid sequence of SEQ ID NO:2;
   c) a nucleic acid molecule which encodes a polypeptide comprising an amino acid sequence a: least 90% identical to the amino acid sequence of SEQ ID NO:2, wherein the polypeptide has kinase activity; and
   d) a nucleic acid molecule which encodes a polypeptide comprising an amino acid sequence a least 90% identical to the amino acid sequence of SEQ ID NO:2, wherein the polypeptide is a non-functional variant of the polypeptide of 1b) or 1c).

2. The nucleic acid molecule of claim 1 further comprising vector nucleic acid sequences.

3. The nucleic acid molecule of claim 1 further comprising nucleic acid sequences encoding a heterologous polypeptide.

4. A host cell which contains the nucleic acid molecule of claim 1.

5. The host cell of claim 4 which is a mammalian host cell.

6. A non-human mammalian host cell containing the nucleic acid molecule of claim 1.

7. A method for producing a polypeptide selected from the group consisting of:
   a) a polypeptide comprising the amino acid sequence of SEQ ID NO:2;
   b) a polypeptide comprising an amino acid sequence which is at least 90% identical to the amino acid sequence of SEQ ID NO:2, wherein the polypeptide has kinase activity; and
   c) a polypeptide comprising an amino acid sequence which is at least 90% identical to the amino acid sequence of SEQ ID NO:2,wherein the polypeptide is a non-functional variant of the polypeptide of 7a) or 7b);

comprising culturing die host cell of claim 4 under conditions in which die nucleic acid molecule is expressed.

8. A kit comprising a nucleic acid molecule of claim 1, or a complement thereof, and instructions for use.

9. A host cell which expresses the nucleic acid molecule of claim 1.

10. The host cell of claim 9, which is a mammalian host cell.

11. A host cell which contains die nucleic acid molecule of claim 3.

12. A host cell which expresses the nucleic acid molecule of claim 3.

13. The nucleic acid molecule encoding the polypeptide of claim 1d), wherein said polypeptide has a substitution for amino acid K-548 of SEQ ID NO:2.

14. The nucleic acid molecule encoding the polypeptide of claim 1d), wherein said polypeptide has a substitution for amino acid D-655 of SEQ ID NO:2.

15. An isolated nucleic acid molecule, consisting of a nucleic acid sequence selected from the group consisting of:
   a) SEQ ID NO:1;
   b) SEQ ID NO:3; and
   c) a nucleic acid molecule which encodes a polypeptide having an amino acid sequence consisting of SEQ ID NO:2.

* * * * *